US011566212B2

(12) United States Patent
Bigliardi et al.

(10) Patent No.: US 11,566,212 B2
(45) Date of Patent: Jan. 31, 2023

(54) INTEGRATED MICROFLUIDIC SYSTEM FOR CULTURING AND TESTING

(71) Applicant: AGENCY FOR SCIENCE, TECHNOLOGY AND RESEARCH, Singapore (SG)

(72) Inventors: Paul Bigliardi, Singapore (SG); Zhiping Wang, Singapore (SG); Ruige Wu, Singapore (SG); Massimo Alberti, Singapore (SG); Bo Wu, Singapore (SG); Mei Bigliardi-Qi, Singapore (SG); Sriram Gopu, Singapore (SG); Srinivas Ramasamy, Singapore (SG); Yuri Hebert Dancik, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 990 days.

(21) Appl. No.: 16/324,571

(22) PCT Filed: Aug. 10, 2017

(86) PCT No.: PCT/SG2017/050400
§ 371 (c)(1),
(2) Date: Feb. 11, 2019

(87) PCT Pub. No.: WO2018/030958
PCT Pub. Date: Feb. 15, 2018

(65) Prior Publication Data
US 2019/0177678 A1 Jun. 13, 2019

(30) Foreign Application Priority Data
Aug. 10, 2016 (SG) .......................... 10201606627Q

(51) Int. Cl.
B01L 7/00 (2006.01)
C12M 3/06 (2006.01)
(Continued)

(52) U.S. Cl.
CPC ....... C12M 23/16 (2013.01); B01L 3/502715 (2013.01); B01L 3/502753 (2013.01);
(Continued)

(58) Field of Classification Search
None
See application file for complete search history.

(56) References Cited

U.S. PATENT DOCUMENTS 2,014,220 A 9/1935 Asmussen
2004/0077075 A1 4/2004 Jensen et al.
(Continued)

FOREIGN PATENT DOCUMENTS

CN 103451090 A 12/2018
DE 20312088 U1 12/2004
(Continued)

OTHER PUBLICATIONS

Qasem Ramadan et al: "In vitro micro-physiological immune-competent model of the human skin", Lab On a Chip, vol. 16, No. 10, Jan. 1, 2016 (Jan. 10, 2016), pp. 1899-1908, XP055669418, ISSN: 1473-0197, DOI: 10.1039/C6LC00229C.
(Continued)

Primary Examiner — Jyoti Nagpaul
(74) Attorney, Agent, or Firm — Troutman Pepper Hamilton Sanders LLP

(57) ABSTRACT

The present disclosure describes a microfluidic chip for culturing and in vitro testing of 3D organotypic cultures. The tests may be performed directly on the organotypic culture in the microfluidic chip. The microfluidic chip includes at least one microfluidic unit which includes two fluidic com-
(Continued)

partments, such as upper and lower, separated by a permeable supporting structure, one or more access opening for the fluidic compartments, and a set of lids interchangeable with a set of insets. The permeable support structure serves as a support for the organotypic culture. The upper and lower compartments may include inlets and outlets which allow fluids to be perfused into the lower compartment and fluids to be perfused into the upper compartment. The access opening may be closed with a lid or accommodate an inset.

17 Claims, 19 Drawing Sheets

(51) Int. Cl.
  *C12M 3/00*    (2006.01)
  *C12M 1/00*    (2006.01)
  *C12M 1/12*    (2006.01)
  *C12M 1/42*    (2006.01)
  *B01L 3/00*    (2006.01)
  *B01L 9/00*    (2006.01)
  *G01N 33/50*   (2006.01)
  *C12N 5/00*    (2006.01)
  *C12N 5/071*    (2010.01)

(52) U.S. Cl.
  CPC ......... *B01L 3/502761* (2013.01); *B01L 3/565* (2013.01); *B01L 7/00* (2013.01); *B01L 9/527* (2013.01); *C12M 21/08* (2013.01); *C12M 23/34* (2013.01); *C12M 25/02* (2013.01); *C12M 29/10* (2013.01); *C12M 35/08* (2013.01); *C12N 5/0062* (2013.01); *C12N 5/0698* (2013.01); *G01N 33/50* (2013.01); *G01N 33/5014* (2013.01); *B01L 2300/0681* (2013.01); *B01L 2300/0861* (2013.01); *B01L 2300/10* (2013.01); *C12N 2513/00* (2013.01)

(56) References Cited

U.S. PATENT DOCUMENTS

2013/0240073 A1*   9/2013   Xia ...................... G05D 7/012
                      137/843
2013/0295551 A1    11/2013   Eddington et al.

FOREIGN PATENT DOCUMENTS

| KR | 10-20080097883 A | 11/2008 |
|---|---|---|
| WO | 03093406 A2 | 11/2003 |
| WO | 2013085909 A1 | 6/2013 |
| WO | 2015027186 A1 | 2/2015 |

OTHER PUBLICATIONS

M. Alberti et al: "Multi-chamber microfluidic platform for high-precision skin permeation testing", Lab On a Chip, vol. 17, No. 9, Jan. 1, 2017 (Jan. 1, 2017), pp. 1625-1634, XP055669400, ISSN: 1473-0197, DOI: 10.1039/C6LC01574C.

Gopu Sriram et al: "Full-thickness human skin-on-chip with enhanced epidermal morphogenesis and barrier function", Materials Today, vol. 21, No. 4, 1 May 20-18 (May 1, 2018), pp. 326-340, XP055655212, Amsterdam, NL; ISSN: 1369-7021, DOI: 10.1016/j.mattod.2017.11.002.

Supplementary European Search Report dated Nov. 13, 2020 issued in European Patent Application No. 17839932.5 (dated Nov. 13, 2020) (13 pages).

Hasan Erbil Abaci et al, "Pumpless microfluidic platform for drug testing on human skin equivalents", Lab Chip. Feb. 7, 2015, 882-888, 15(3).

International Search Report for PCT/SG2017/050400, 7 Pages.

* cited by examiner

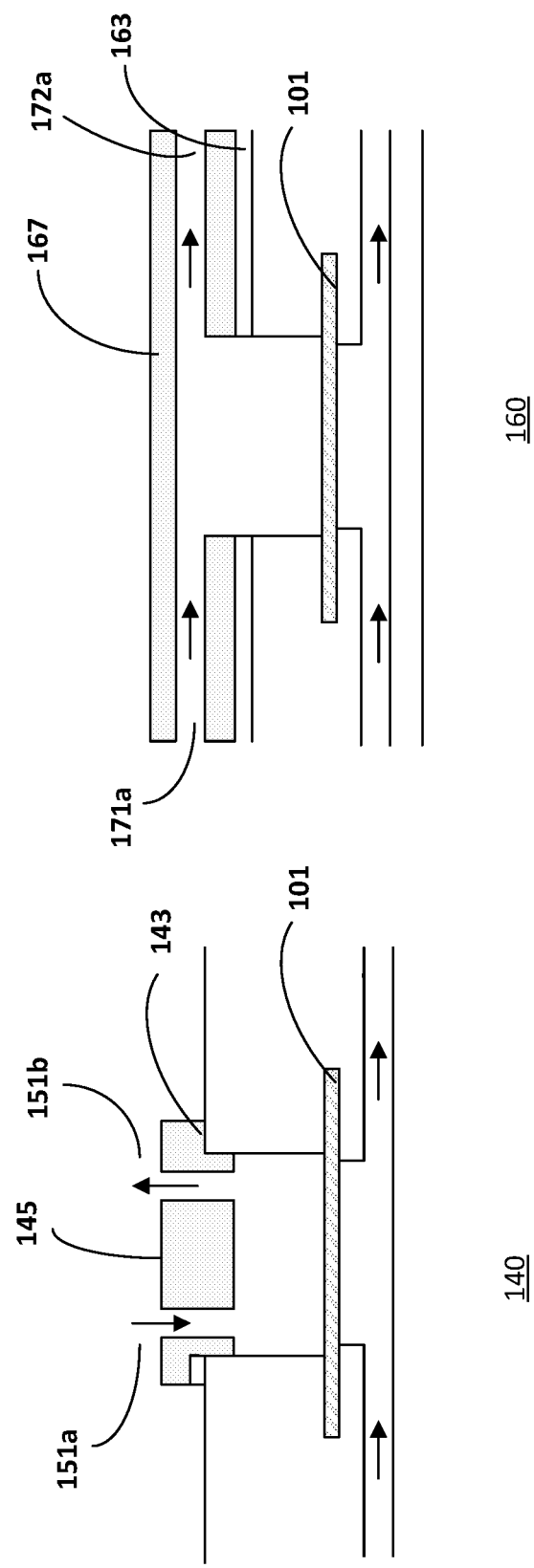

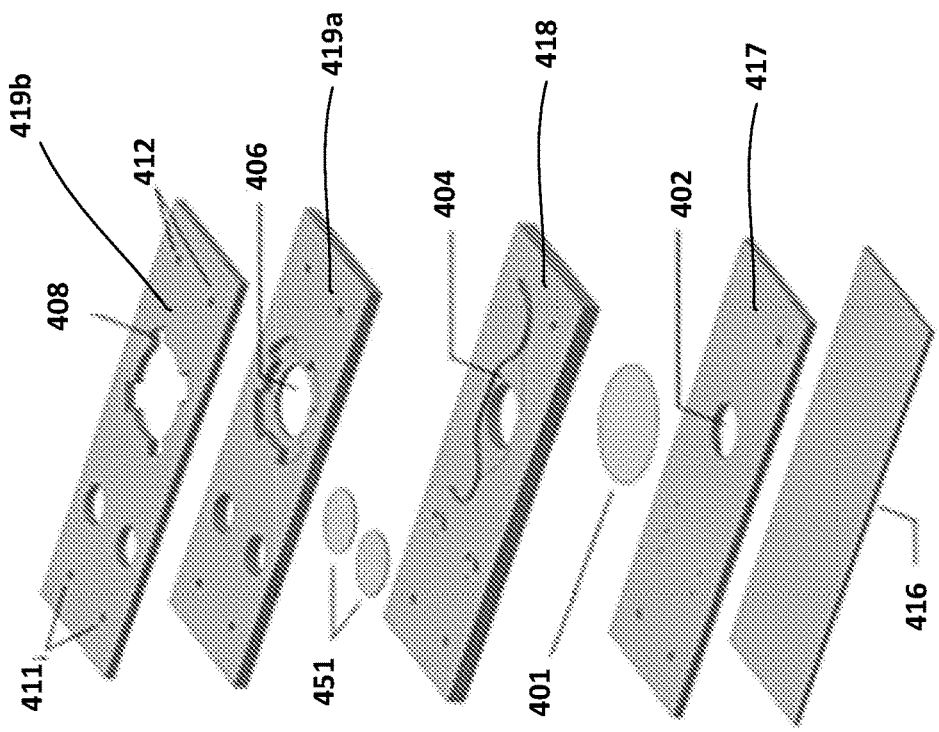
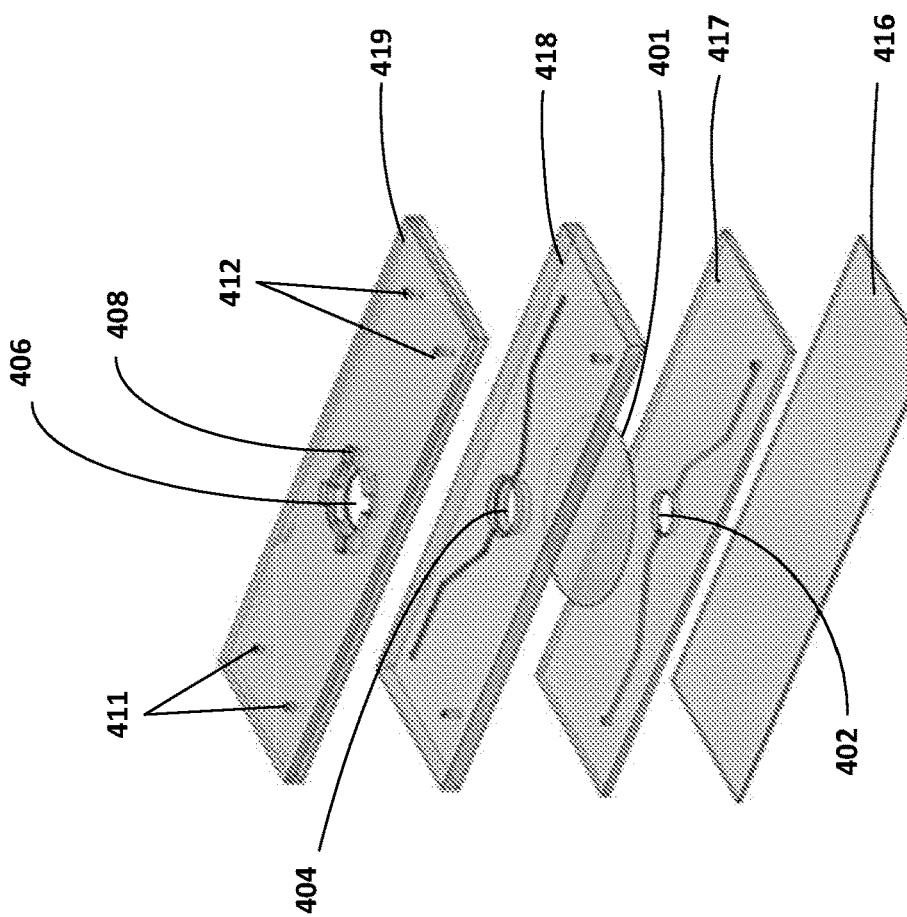
Fig. 4a
Fig. 4b

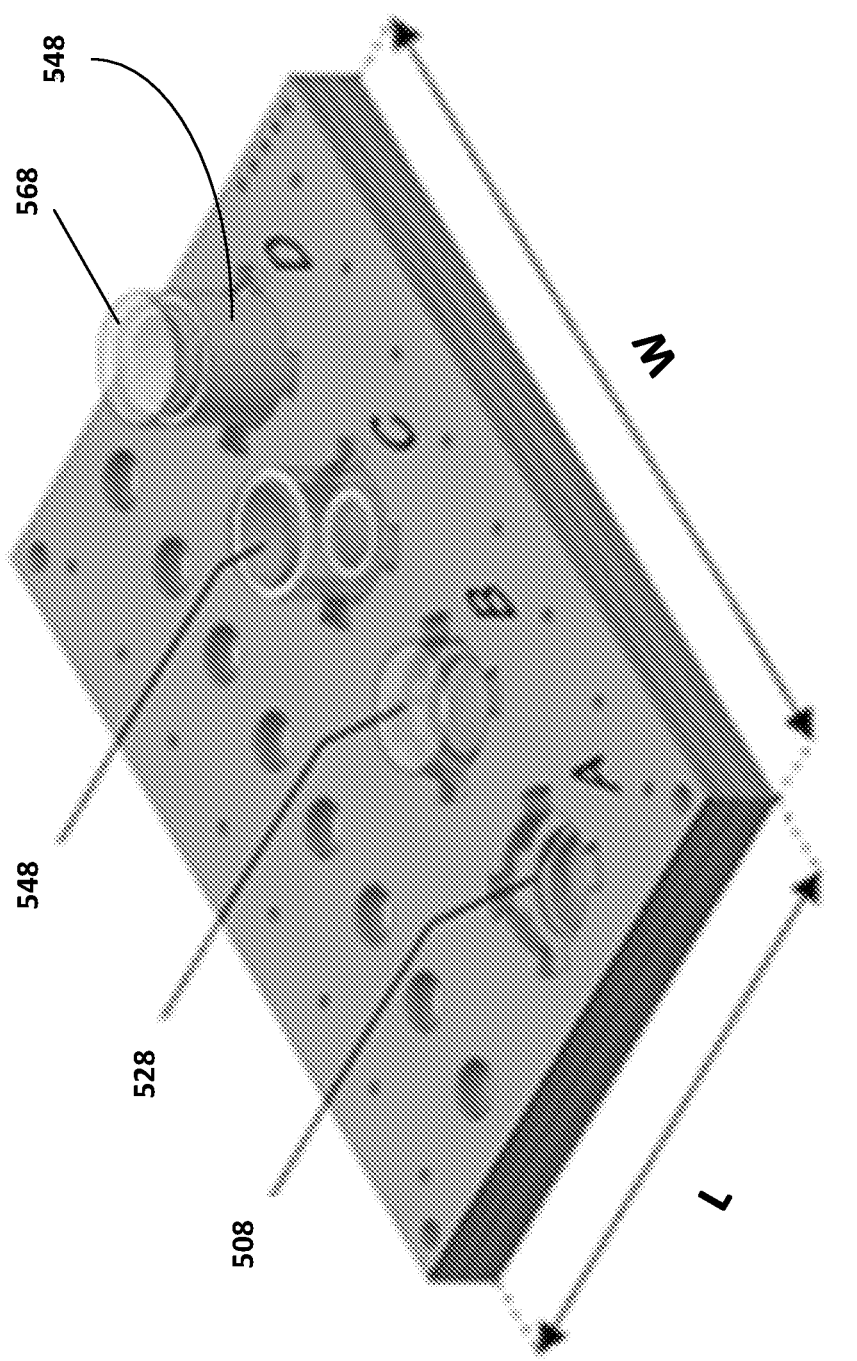

620

600

660

640

690

680

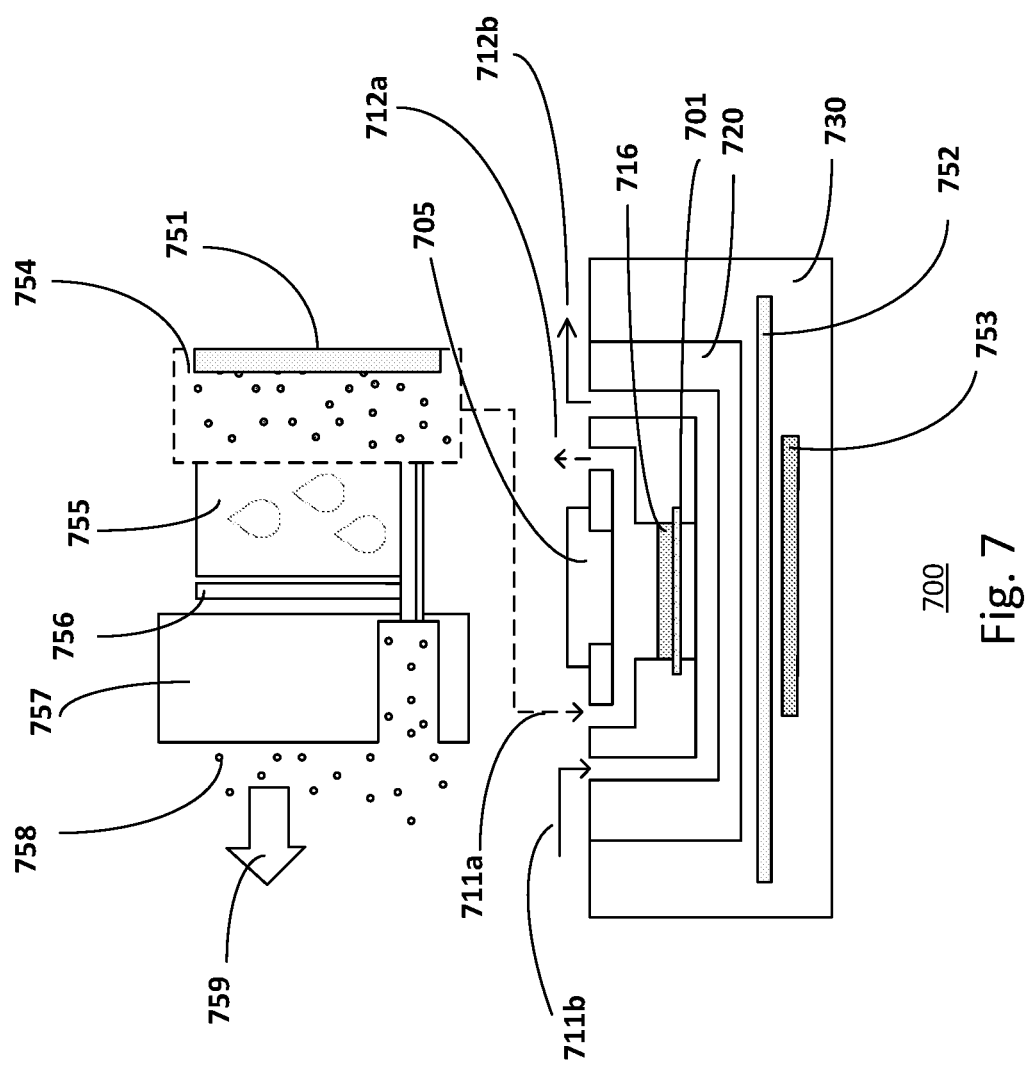

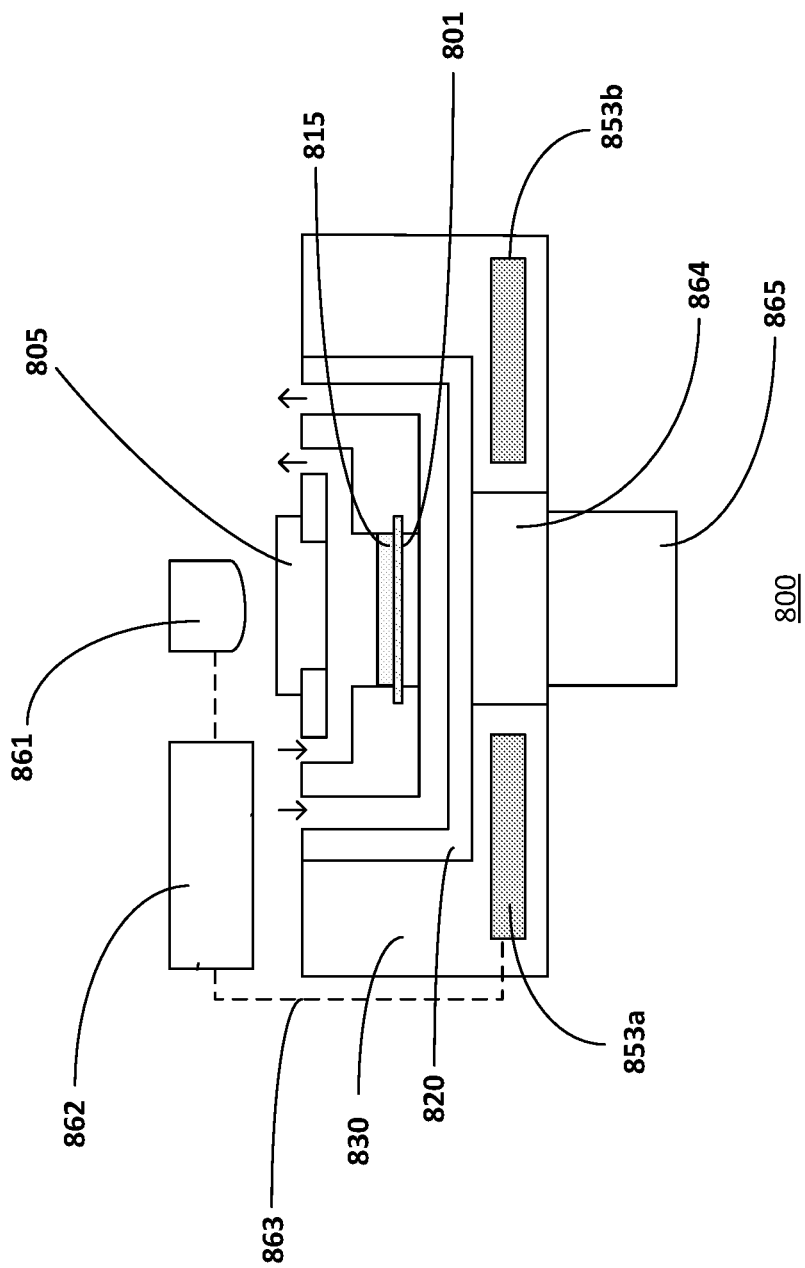

1200

1250

INTEGRATED MICROFLUIDIC SYSTEM FOR CULTURING AND TESTING

TECHNICAL FIELD

The present application relates to microfluidic system for integrated culturing and in vitro testing of three-dimensional organotypic cultures.

This application claims priority to Singapore Patent Application No. 10201606627Q, filed on Aug. 10, 2016, which is herein incorporated by reference in its entirety for all purposes.

BACKGROUND

Three-dimensional (3D) human skin equivalent (HSE) research has gained importance as an alternative to replace animal testing in cosmetic, pharmacological and toxicological sciences. Three-dimensional HSEs, which derived from human cell lines, can mimic native skin's cellular organization and function, lipid composition and differentiation, metabolic capability, and retain apical polarization in basal keratinocytes. Human skin equivalents may either be reconstructed human epidermis (RHE), which includes the stratum corneum and the viable epidermis, or full-thickness skin equivalents (SEs), which include the same layers above a dermal equivalent (DE).

Although the skin's main barrier to percutaneous penetration resides in the stratum corneum, with the viable epidermis providing an additional barrier for lipophilic chemicals, the presence of the dermal layer in SEs is deemed necessary for superior skin homeostasis due to the interaction between the dermal fibroblasts and epidermal keratinocytes. However, obstacles exist in hampering the quality and reproducibility of SEs. Such obstacles include the amount of obtainable samples from donor biopsies, low propagation in culture, contraction of the DE and inferior barrier function which limit their utility in percutaneous penetration and toxicity studies.

RHE and SE are conventionally reconstructed on tissue culture inserts. Microfluidics technology has also been employed in producing 3D organotypic cultures. However, in these microfluidic devices, SEs are either not reconstructed directly in the microfluidic system, hence they do not take advantage of the benefits of dynamic culture, or do not represent the 3D complexity of human skin. Moreover, conventional technologies and methods focusing on skin permeation are relatively expensive and have low throughput in producing SE cultures.

The present disclosure is directed to a low cost microfluidic platform focusing on skin permeation with high precision and high throughput. Furthermore, the microfluidic platform includes an integrated culturing and testing microfluidic chip that enables improved morphogenesis and differentiation of the cultured tissue.

SUMMARY

Embodiments generally relate to a platform for culturing and in vitro testing organotypic culture and a method thereof. In one embodiment, a microfluidic chip is disclosed. The microfluidic chip includes a chip body having a cavity disposed in the chip body. A permeable support separates the cavity into first and second fluidic compartments. The chip body comprises a first cavity access opening for accessing the first fluidic compartment. A first set of fluidic channels is in fluidic communication with the first fluidic compartment. The first set of fluidic channels includes at least one first inlet channel and at least one first outlet channel. The first set of fluidic channels is adapted to flow a first fluid into the first fluidic compartment via the first inlet channel and out the first fluidic compartment via the first outlet channel. A second set of fluidic channels is in fluidic communication with the second fluidic compartment. The second set of fluidic channels includes at least one second inlet channel and at least one second outlet channel. The second set of fluidic channels is adapted to flow a second fluid into the second fluidic compartment via the second inlet channel and out the second fluidic compartment via the second outlet channel. The microfluidic chip further includes a chip temperature control unit in the chip holder for controlling a temperature of the microfluidic chip when mounted onto the chip holder, and a thermal-electrical-cooling unit for controlling humidity of the atmosphere in the test chamber.

With these and other advantages and features that will become hereinafter apparent, further information may be obtained by reference to the following detailed description and appended claims, and to the figures attached hereto.

BRIEF DESCRIPTION OF THE DRAWINGS

Some embodiments are illustrated in the accompanying figures, in which like reference numerals designate like parts, and wherein:

FIGS. 1a-1d show exemplary embodiments of microfluidic chips;

FIGS. 4a-4b show exploded views of embodiments of microfluidic chips;

FIG. 5 shows an exemplary embodiment of a multi-chamber microfluidic chip;

FIG. 7 shows a micro-environmental parameter control system for use with the microfluidic chip;

FIG. 8 shows another embodiment of a control system for use with the microfluidic chip;

DETAILED DESCRIPTION

Figure 1B:
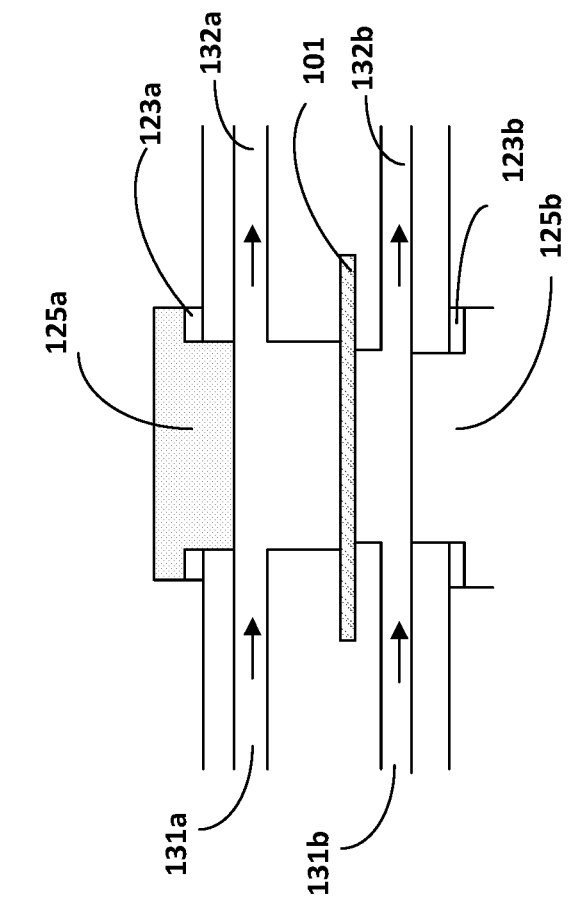

The disclosure relates to a microfluidic chip, for example, an organ-on-chip device for a miniature organotypic model. The microfluidic chip serves as a platform for culturing 3D organotypic culture and for performing in vitro tests. The tests may be performed directly on the organotypic culture in the microfluidic chip. For example, microfluidic chip may integrate both culturing and testing of a 3D organotypic culture on the same chip.

The microfluidic chip includes at least one microfluidic unit, which includes two fluidic compartments, such as upper and lower compartments, separated by a permeable supporting structure. The permeable support structure serves as a support for the organotypic culture. In one embodiment, the upper and lower compartments may include inlets and outlets. For example, the inlet and outlet of the lower compartment allow fluid to perfuse into the lower compartment on the lower side of the permeable supporting structure while the inlet and outlet of the upper compartment allow fluid to perfuse into the upper compartment on the upper side of the permeable supporting structure.

A fluidic compartment may include an access opening, opposite to the permeable supporting structure, that allows manual casting of the extracellular matrix, manual cell seeding, and insertion of or connection to other modules in the chamber for performing in vitro tests. In some cases, only one fluidic compartment, such as the upper compartment, may include an access opening. Providing other configurations of the fluidic compartments may also be useful. For example, the lower compartment or both upper and lower compartments may include access openings.

The microfluidic chip may include a set of interchangeable lids or covers for covering the access opening. The lid or cover may be adapted to ensure proper sealing. For example, the lid may be made of a sealing material or may include a sealing gasket or O-ring. Different mechanical principles or techniques, such as self-locking mechanism, clamping mechanism, spring-loaded mechanism, sliding mechanism, screwing mechanism as well as other types of mechanical techniques, may be used to provide adequate pressure to the lid or cover in order to achieve adequate sealing. The inlet and outlet channels of the fluidic compartments may be structured or configured either inside the bulk or body of the microfluidic chip or in the lid or cover.

As discussed, the microfluidic chip includes a chamber which may be used for culturing 3D organotypic culture. The compartments, such as the upper and lower compartments may be configured with small or minimal volumes, providing a dynamic environment suitable for automation and precise controlling of the micro-environment. Furthermore, the microfluidic chip enables for high-throughput, standardized and reliable in vitro tests on organotypic cultures. In addition, the microfluidic chip may be adapted to provide standardized flow rates and to deliver cells and test compounds into the chambers of the chip or chips through a tube system. Cells and test compounds in liquid or gas form may be provided through the tube system in a controlled environment.

Figure 1A:
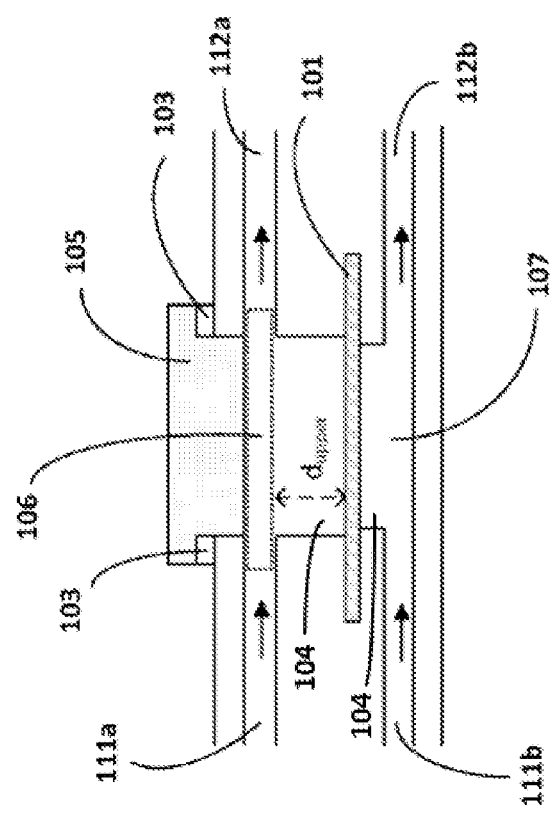

FIGS. 1a-1d show various embodiments of microfluidic chips or units. Referring to FIG. 1a, a microfluidic chip 100 with two compartments is shown. The microfluidic chip 100 has a cavity 104. For example, the two compartments are the upper and lower fluidic compartments. A permeable supporting structure 101 separates the cavity 104 into the two fluidic compartments and defines the two fluidic compartments. The microfluidic chip includes one access opening. The access opening is covered by a cover or lid 105. Gasket 103 may be included to ensure proper sealing of the access openings. Inlet 111a-b and outlet 112a-b channels are structured in the bulk of the microfluidic chips. The direction of fluid flow in the two channels is indicated by the arrow, from the inlet to the outlet.

The microfluidic chip 100 includes two compartments. For example, the two compartments are the upper and lower fluidic compartments. The first compartment may include a first well and the second compartment may include a second well. The first or upper well may have a depth ($d_{upper}$) of about 1.5 mm for tissue culture purposes. Providing other depths of compartments may also be useful. The first or upper compartment may include an upper or apical chamber 106 which may be used for perfusion of tissue or solution or gases or cell suspensions, depending on the application. For example, the upper or apical chamber 106 is the area above the first well. In addition, the apical chamber may be configured for controlling shear stress acting on the surface of the tissue culture. The design of the apical chamber may determine a homogenous distribution of shear stresses acting on the apical side of the tissue culture and a homogeneous cell seeding. The second or lower compartment includes a lower or basal chamber 107 which is intended for perfusion of tissue or solution depending on the applications.

The pressure gradient generated across the tissue culture by the fluidic flow in the compartments during the culture may increase interstitial flow in the culture sample. Interstitial flow may enhance the transport of nutrients in the chip and may induce morphogenetic effects in culture sample as a result of shear stresses and other mechanotransduction mechanisms.

A permeable supporting structure 101 separates and defines the two compartments. The permeable supporting structure includes first and second surfaces, one facing the first compartment and the other facing the second compartment. Pore size of the permeable supporting structure may be selected to prevent undesired cell migration through it. Alternatively, the pore size of the permeable supporting structure may be selected to allow cell migration through it.

Inlet 111a and outlet 112a channels are structured in the bulk of the microfluidic chip, for example, in the upper compartment. Inlet 111b and outlet 112b channels are structured in the bulk of the microfluidic chip, for example, in the lower compartment. The direction of fluid flow is indicated by the arrow, from the inlet channel to the outlet channel. The flow of media through the microfluidic compartments provides a continuous supply of nutrients and simultaneous removal of metabolic waste products, similar to the role of blood vessels in native human tissues and organs.

The microfluidic chip 100 includes one access opening. The access opening is located, for example, in the upper compartment. The access opening may be covered by a cover or lid 105. A gasket or O-ring 103 may be included to ensure proper sealing of the access openings.

In one embodiment, as shown in FIG. 1B, a microfluidic chip 120 is designed with two access openings. The microfluidic chip is similar to that described in FIG. 1a, common elements may not be described or described in detail. A first access opening may be located in the upper compartment and a second access opening may be located in the lower compartment. The access opening may be covered by a cover or lid 125a/b and a gasket or O-ring 123a/b. As shown, inlet 131a/b and outlet 132a/b channels are provided for the first and second compartments. Microfluidic chips with two access openings, for example, are advantageous for co-culture of organotypic tissues that requires gel casting or scaffolds on the opposite sites of the supportive structure 101.

The wells of the compartments, for example, the first or apical well of the first or upper compartment shown in FIGS. 1a-1b, may be a cylindrical well that provides a mold for the tissue culture. For example, the base of the first well is delimited or defined by one or a first surface of the permeable supporting structure while the base of the second well is defined by the other or a second surface of the permeable supporting structure. Other configurations and geometries of the wells may be useful.

FIGS. 1c-1d show examples of alternative embodiments of the microfluidic unit wherein the inlet and outlet channels of one compartment are structured in different parts of the microfluidic chip. The microfluidic chip is similar to that described in FIGS. 1a-1b, common elements may not be described or described in detail.

As shown in FIG. 1c, the inlet 151a and outlet 151b channels of the first compartment are structured in the lid 145 of the microfluidic chip 140. The lid 145 closes and seals the access opening in the first compartment. A gasket or O-ring 143 may be included to ensure proper sealing of the lid. In another embodiment, as shown in FIG. 1d, the inlet 171a and outlet 172a channels are structured in the cover 167 of the microfluidic chip 160. The cover 167 closes and seals the access opening in the first compartment. A gasket or O-ring 163 may be included to ensure proper sealing of the lid. In the case of testing of liquid formulations with low viscosity, providing the microfluidic chip 140 or 160 with inlet and outlet channels is advantageous for automating the "posology", for example for precise and controllable temporal, spatial and volumetric dosage.

Penetration or toxicology tests may be performed directly on the organotypic tissue cultured on the microfluidic chips as described in FIGS. 1a-1d. The advantage is that in vitro test is performed on the same platform where the tissue is reconstructed, without displacing and transferring the tissue to a different apparatus. The microfluidic chip enables conducting assays for penetration, absorption, irritation and toxicology without displacing or manipulating the organotypic culture.

Figure 2B:
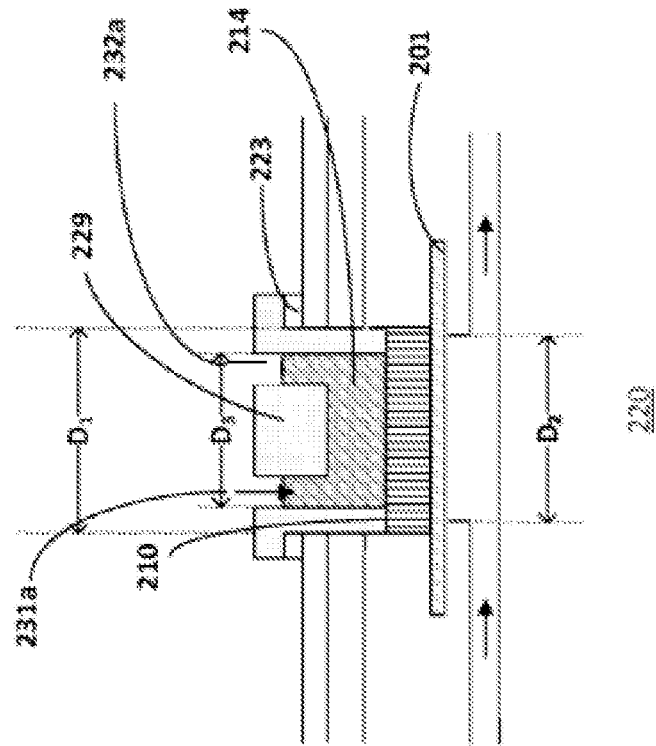
FIGS. 2a-2b show exemplary embodiments of insets for microfluidic chips.
Figure 2A:
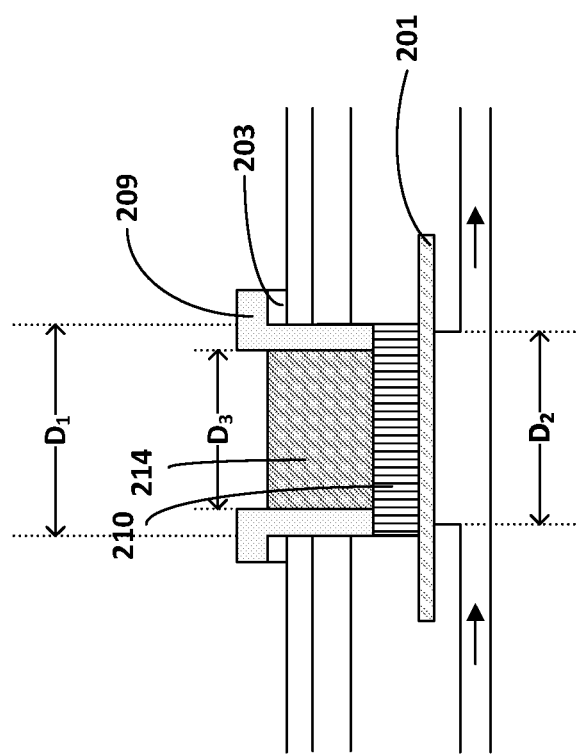

FIGS. 2a-2b show exemplary embodiments of insets for microfluidic chips. The insets, for example, enable alternative setups for the microfluidic chip. The insets, for example, are interchangeable with the lid or cover. For example, the insets are compatible with the access opening and with the locking and sealing mechanism 203, 223 of the microfluidic chip. An inset may be used to define the application chamber and to clamp and seal the edges of the cultured tissue to avoid undesired penetration of the compound to be tested through eventual gaps existing between the tissue culture and the walls of the culture well. The inset also allows placing a protective material on the cultured tissue and studying its influence on the in vitro test results.

In one embodiment, the inset 209 is an open well, as shown in FIG. 2a, for manual application of the compound to be tested. In another embodiment, the inset 229 may be provided with inlet 231a and outlet 232a channels, as shown in FIG. 2b, for automated application when solutions with low viscosity are applied in the application chamber.

In one embodiment, the upper compartment may serve as the application chamber. In one embodiment, the diameter of the culturing well ($D_1$) where the inset for in vitro tests is introduced may be larger than the diameter of the well on the other side of the supporting structure 201 ($D_2$) in order to provide a rigid base surface for the inset 209/229 and to properly seal the edges of the organotypic culture. This may be advantageous, particularly if the culture supporting structure is made of a fragile material. In another embodiment, the diameter of the application chamber ($D_3$) defined by the inset 209/229 for in vitro test may be smaller than the diameter of the well on the other side of the supporting structure ($D_2$). This is advantageous since it improves penetration accuracy of the applied compound in the lower compartment.

The compound or agent to be tested 214 may be applied to the tissue culture 210 from one of the fluidic compartments. For example, the compound or agent may be applied to the application chamber. For example, the compound or agent may be applied from the inlet of one of the fluidic compartments. Other configurations of providing the compound or agent may also be useful. The microfluidic chip 200 with the open inset is advantageous for applying formulations with high viscosity, such as topical formulation, creams, solids, semi-solids. In the case of testing of liquid formulations with low viscosity, providing the microfluidic chip 220 with inlet and outlet channels is advantageous for automating the "posology", for example for precise and controllable temporal, spatial and volumetric dosage.

Figure 3B:
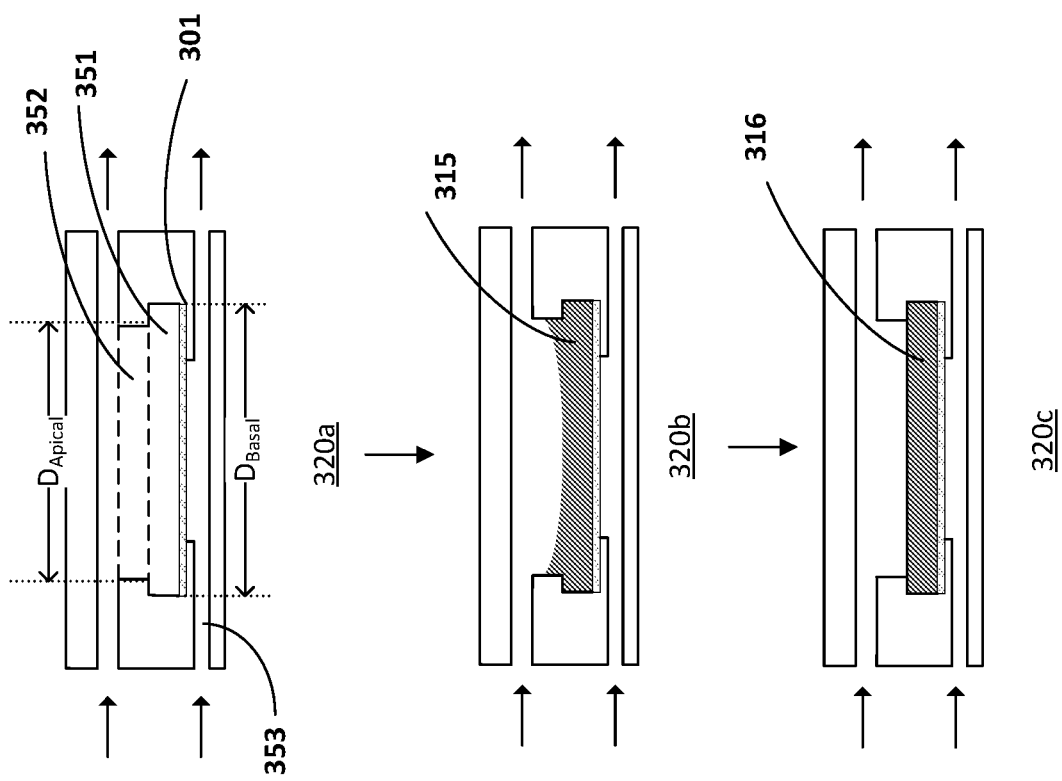
FIGS. 3a-3b illustrate other embodiments of microfluidic chips with gel casting chambers.
Figure 3A:
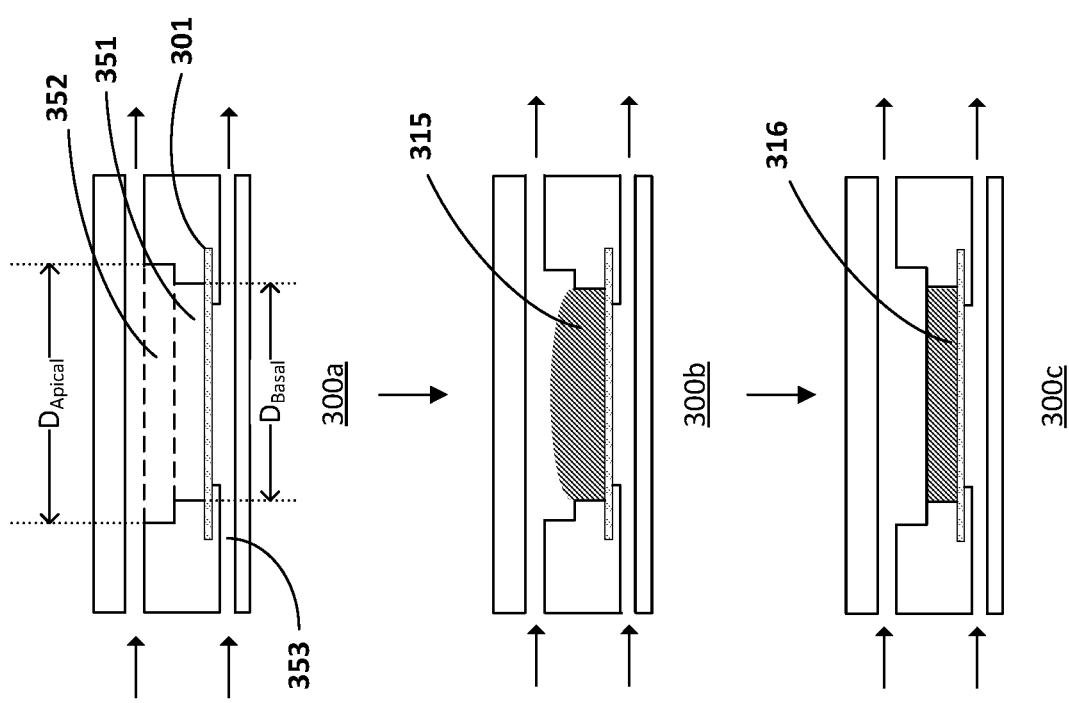

FIGS. 3a-3b show alternative embodiments of culturing units. For example, a culturing unit may include an upper compartment with a first well having a basal sub-chamber 351 with a predetermined height and an apical sub-chamber 352, and a lower compartment 353. The apical sub-chamber 352 connects to the inlet and outlet channels of the upper compartment. The supporting structure 301 defines the base of the basal sub-chamber. The basal sub-chamber may house a gel/matrix 315 or the first component of a multi-layered co-culture. The base of the basal sub-chamber ($D_{Basal}$) of the microfluidic chip 300a-c may be smaller than the base of the apical sub-chamber ($D_{Apical}$), as shown in FIG. 3a (300a). Alternatively, the base of the basal sub-chamber ($D_{Basal}$) of the microfluidic chip 320a-c may be larger than the base of the apical sub-chamber ($D_{Apical}$), as shown in FIG. 3b (320a).

The partition in two chambers is dimensioned to aid the casting of the gel. As shown in the FIG. 3a (300b), the gel/matrix 315 is deposited in the basal sub-chamber so that a convex meniscus of gel is formed at the pre-determined height. When the gel contracts during the culturing process (300c), the meniscus 316 flattens down. For example, the contact angle with the wall of the basal sub-chamber decreases, ideally till it is 90° or horizontal, and therefore provides a flat surface for a homogeneous seeding of the next cell layer.

As shown in FIG. 3b (320b), the gel is deposited in the basal sub-chamber so that a concave meniscus of gel is formed at the pre-determined height. When the gel contracts during the culturing process (320c), the meniscus 316 flattens down. For example, the contact angle with the wall of the basal sub-chamber decreases, ideally till it is 90° or horizontal, and therefore provides a flat surface for a homogeneous seeding of the next cell layer. The volume of dermal matrix cast in the well is optimized to guarantee a flat apical surface of culture sample. This, together with an optimized design of the upper compartment improves the consistency of cell seeding and reduces epithelial leaks or edge damages. For example, the tissue culture and diffusion areas are of 0.4 $cm^2$ or 0.2 $cm^2$.

In one embodiment, in its in vitro assay system configurations as shown in FIG. 2a-b, the application chamber of the assembled device has capacities of up to 2000 μL and receiver volumes (the basal chamber of the lower compartment) of up to 1000 μL. For example, the application chamber may be configured to accommodate 500 μL of solution and the basal chamber may be configured to accommodate at least 28 μL of solution. Although exemplary configurations of the chambers are provided, it should be understood that other dimensions, volumes and configurations of chambers may also be useful.

FIGS. 4a-4b show exploded perspective views of embodiments of a microfluidic chip. FIG. 4a shows a fundamental unit of a microfluidic chip. The microfluidic chip 400 includes 4 layers, a transparent base layer 416, a lower compartment layer 417, an upper compartment layer 418, and a top layer 419. The top layer may include inlets 411 and outlets 412, an access opening 406 and a locking station 408. The permeable supporting structure 401 is structured between the upper compartment 404 and the lower compartment 402 between the lower compartment layer 417 and the upper compartment layer 418. Each fluidic compartment has dedicated inlets and outlets that are used for perfusion of culture media, liquids or gaseous mixtures, for inoculation of cells, and for insertion of electrodes.

A microfluidic chip may include additional components. For example, as shown in FIG. 4b, a top layer of the microfluidic chip 420 may include 2 layers 419a and 419b. The two top layers contain structures for the access opening and locking station for a lid or inset. The access opening and locking station are aligned with the well of the corresponding compartment, i.e. with the culture chamber, thus enabling direct casting of culture sample on the support membrane. Other configurations of the top layer may also be useful.

The microfluidic chip 420 may also include inline de-bubbling units. For example, the de-bubbling unit or de-bubbler may be an active or passive bubble trap, a vacuum-driven degasser, or a membrane-based bubble removal system. For example, the de-bubbling units may include selective de-bubbling membranes 451. The de-bubbling membranes are located between the upper compartment layer 418 and the top layer 419 at where the fluidic channels pass through. For example, the de-bubbling membranes integrate de-bubbling structures or de-bubblers in the inlet channels of the underneath two compartments. The de-bubbling unit or de-bubbler is integrated along each inlet channel to prevent bubbles from reaching the basal and apical chambers. The de-bubbling unit or de-bubbler reduces the risks associated with bubbles in the culture chamber and high liquid pressure differences across the chip.

Depending on the materials used, different methods for manufacturing the microfluidic chip may be used. Advantageously the blocks of materials that compose the chip and the thin supporting structure are made of plastic material, and they are bonded together by thermal bonding, solvent bonding, ultrasonic bonding, laser bonding, adhesive bonding, or other bonding techniques. Furthermore, electrodes may be inserted, embedded or coated in the lower and in the upper compartment, or on the lids/covers. Providing electrodes may be useful for transepithelial electrical resistance (TEER) application.

In one embodiment, the microfluidic chip is made of thermoplastics. The layers are microstructured poly(methyl methacrylate) (PMMA) layers. The 4 layers may be of different thicknesses. The chip may be processed by a one-step thermal bonding fabrication process. For example, the fluidic features may be fabricated by computer numerically controlled (CNC) micro-milling. The chip may be amenable to mass production techniques such as injection molding and hot embossing. The permeable supporting structure 401 is a microporous polycarbonate (PC) membrane. For example, the microporous track etched PC membranes with 1 μm pore size and pore density of $2 \times 10^6$ pores/cm$^2$ are sandwiched between the second and the third layers, aligned with the microstructures defining the tissue culture chambers. The de-bubbling membranes 451 are polytetrafluoroethylene (PTFE) membranes. For example, circular PTFE membranes with 8 mm diameter were sandwiched between the third and the fourth layers, aligned with the microstructural features of the de-bubbling units. For example, the inlet and outlet channels are 0.5 mm and 1 mm wide respectively and all channels are 0.5 mm high. Although the dimensions of channels are provided as an example, it should be understood that other dimensions of channels may also be useful.

As discussed, the microfluidic chips may have various embodiments for different applications. For example, as already discussed in FIGS. 1a-1d, the access openings may be provided for both the upper and lower compartments. For example, as already discussed in FIGS. 1a-1d and FIGS. 2a-2b, the inlet and outlet channels of the upper and lower compartments may be located at different locations. For example, as already discussed in FIGS. 2a-2b, the base of the well in the upper compartment may be larger than the base of the well in the lower compartment. For example, as already discussed in FIGS. 3a-3b, the base of the apical chamber may be larger than the base of the basal chamber. In another embodiment, the base of apical chamber may be smaller than the base of the basal chamber. Furthermore, the compartments may include various sub-chambers and the structural features of the compartments may be different.

The microfluidic chip, for example, may be used for culturing organotypic skin and for performing penetration tests on the said reconstructed skin. The microfluidic chip, as shown, includes an upper compartment 404 with inlet and outlet channels, intended to either or all of the following: contain the tissue culture during the culturing process, infuse cell suspensions, perfuse with nutrients one side of the tissue culture, perfuse with different fluids (including air) one side of the tissue culture, directly contain the formulation/solution/compounds to be tested and therefore function as an application chamber during the in vitro test, and/or allocate the inset that defines the application chamber during the in vitro test.

A lower compartment 402 with inlet and outlet channels is provided. The lower compartment is intended to either or all of the following: perfuse with nutrients the other side of the tissue culture during the culturing process, and/or contain and perfuse a receptor solution during in vitro testing.

The microfluidic chip also includes a permeable supporting structure 401 (e.g. porous thin membranes, porous thin structured layers, meshes or scaffold, etc.) between the upper and the lower compartments that act as a support for the culture and also allows efficient transport of nutrients, metabolites and test compounds or agents.

The microfluidic chip may include an access opening 406 that allows manual casting of extracellular matrix gel or insertion of scaffolds, with a locking station 408 for a lid or an inset.

FIG. 5 shows an exemplary multi-chamber device. The multi-chamber device includes a plurality of chambers. The chambers may be independent or interconnected or partially interconnected. As shown, the multi-chamber device includes four chambers arranged in 1×4 configuration. Although the multi-chamber device is illustrated as 1×4 configuration, it is understood that other configurations of multi-chambers device may also be useful.

The multi-chamber device has a width (W) and a length (L). The width (W) equals to the total width of the chambers in a column and the length (L) equals to the total length of chambers in a row. In one embodiment, the multi-chamber device has the same type of individual chips. In another embodiment, the multi-chamber device has different types of individual chips. For example, the 4-chamber chip device arranged in 1×4 configuration may have a width (W) of about 75 mm and a length (L) of about 50 mm. Other dimensions of the multi-chamber chip device may also be useful.

The multi-chamber may include chambers with same operation configurations. The multi-chamber device may also include chambers with different operation configurations. For example, the 4-chamber chip device includes 4 operation configurations: (A) an open system with an access opening 508; (B) a bioreactor with an access opening closed by a cover or lid 528; (C) an in vitro analysis system with an inset 548; and (D) another in vitro analysis system with an inset 548 covered by a cap 568. The lids and insets allow easy switching between different configurations without disrupting the tissue cultured in the microfluidic chip or dissembling the microfluidic device. Other configurations may also be useful.

Figure 6B:
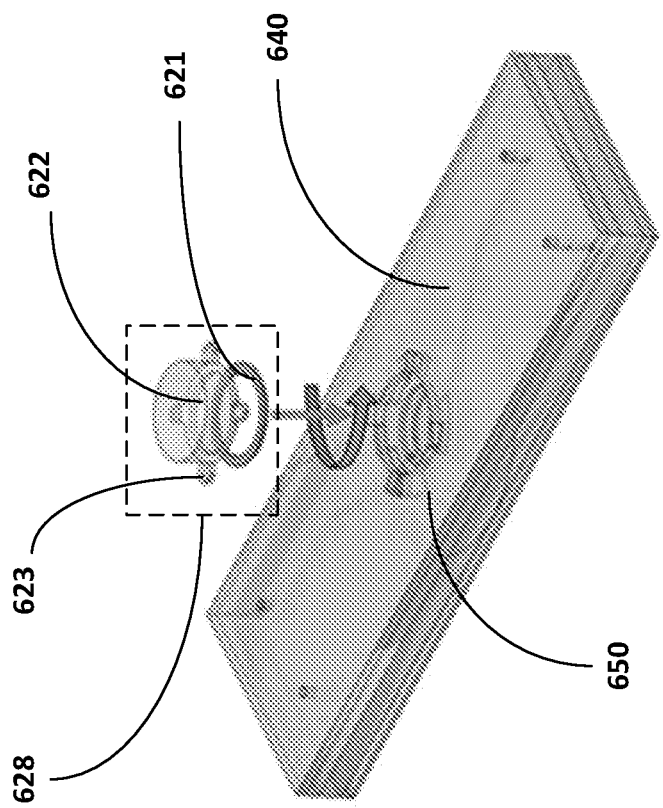
FIGS. 6a-6f show embodiments of microfluidic chips in different operational configurations with a cover, lid or inset.
Figure 6A:
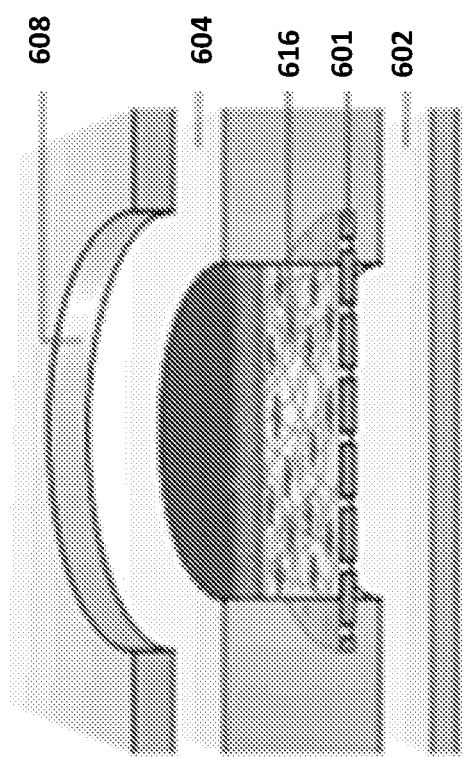

FIGS. 6a-6f illustrate the different operation configurations in detail. For example, FIG. 6a shows an embodiment of an open system 600. The open system includes an access opening 608, an upper compartment 604, a permeable supporting structure 601 and a lower compartment 602. For example, the cell layer 616 has a flattened surface in the basal sub-chamber of the upper compartment. In one embodiment, the cell layer 616 is a skin-equivalent, e.g. an in vitro skin model used to conduct experiments.

FIG. 6b shows an embodiment of a lid for a microfluidic chip. For example, the microfluidic chip 620 is a bioreactor with an access opening closed by a cover or lid 628. The cover or lid includes a self-locking system. For example, the lid may be employed to seal the upper compartment of the microfluidic chip. To ensure sealing, a sealing gasket 621 may be included. The cover provides a closed system during cell culture so that fluids may flow from the inlet to the outlet channels. As shown, the cover is for the upper compartment. Providing a cover with the self-locking system for the lower compartment or both compartments may also be useful.

The cover or lid 628 may be a thick cylindrical body 622 having a number of thin teeth 623 protruding from its lateral surface, perpendicularly to the cylinder axis. The lid may be equipped with a gasket annulus or O-ring 621. The locking station 650 is composed of an equivalent number of slots arranged in a corresponding geometry to the teeth of the lid. Each slot is composed of a vertical entrance for the tooth and a lateral thin chamber, whose height is smaller than the sum of the height of the tooth and the thickness of the gasket; the lid is inserted in the locking structure of the chip by aligning its teeth with the corresponding vertical entrances in the locking station, pressed down and turned clock-wise or counter clock-wise in order to position and maintain the teeth inside the lateral slots, so that the compression of the gasket allows for the lid to be locked and the chamber to be sealed. Other types of lids or locking mechanisms may also be useful.

Figure 6D:
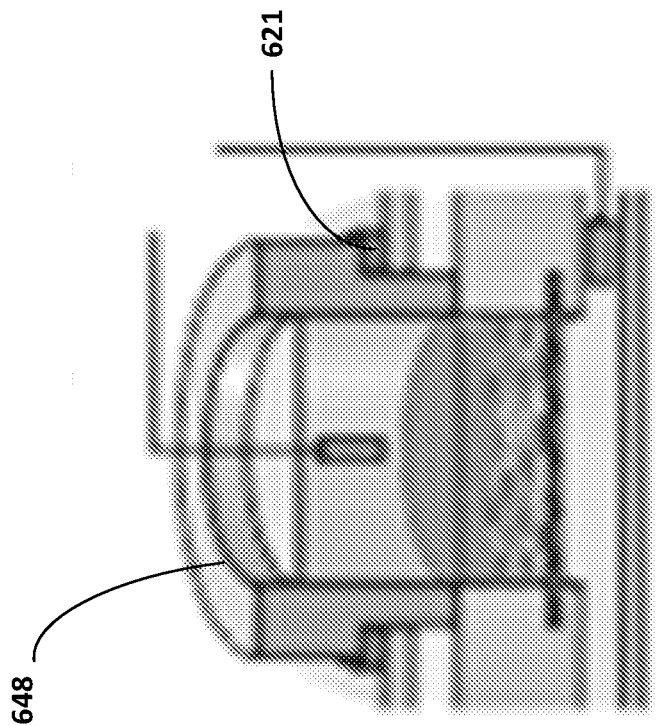
Figure 6C:
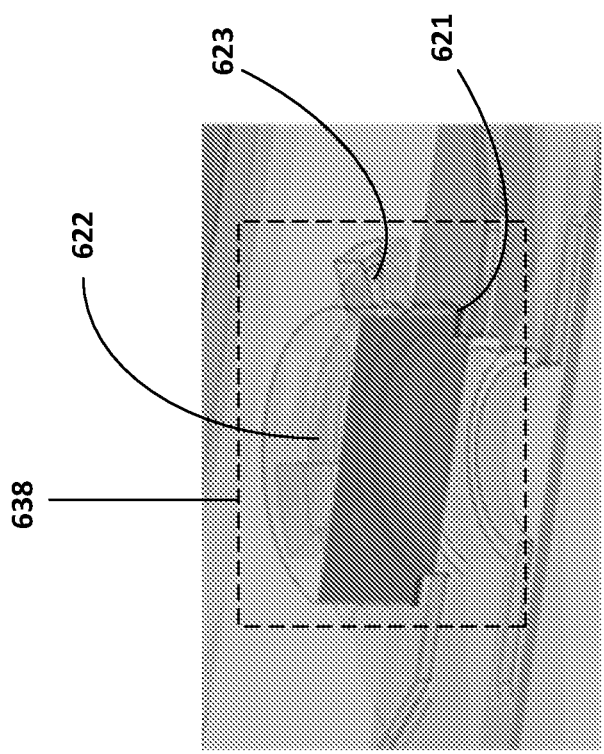

FIG. 6c shows a microfluidic chip 640 with a self-locking lid 638 in locked position. The lid is similar to that described in FIG. 6b, common components may not be described or described in detail. For culturing the organotypic culture, the self-locking lid 638 is assembled to the body of the microfluidic chip. For example, the lid is attached to compartments of the chip. The self-locking lid allows the culture media to flow in the apical chamber of the upper compartment.

FIG. 6d shows a microfluidic chip 660 with an inset 648. For example, the microfluidic chip 660 is an in vitro analysis system for in vitro tests. When the organotypic culture process is completed, the lid is replaced by the inset 648. In some cases, the inset may also be equipped with a sealing gasket 621. The inset may press on the edges of the organotypic culture in order to achieve a leak proof sealing. In some embodiments, the inset and the organotypic culture may be separated by a gasket annulus or O-ring for achieving the proper sealing. The inset defines a donor compartment and allows direct application of solid and viscous compounds.

Figure 6F:
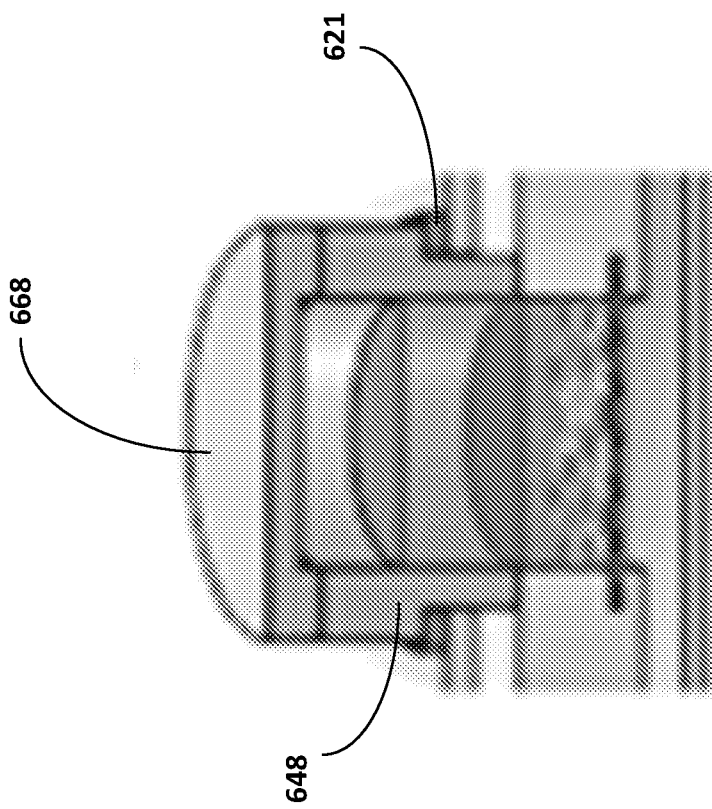
Figure 6E:
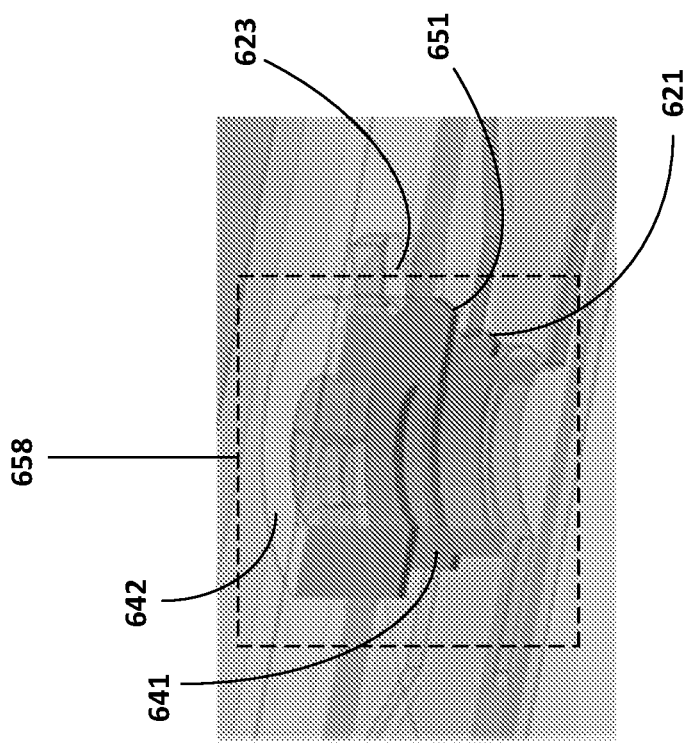

FIG. 6e shows a microfluidic chip 680 with a self-locking multi-component inset 658. For example, the self-locking multi-component inset is a self-locking 2-component inset. The inset is similar to that described in FIG. 6d, common components may not be described or described in detail. For example, the inset may include two parts 641 and 642 separated by another gasket annulus 651. The first part 641 may be a ring that fits in the culture well and is in contact with the edges of the organotypic tissue. The second part 642 may be a clamp that presses on it and that may be locked in the locking station. The gasket annulus 651 may be provided to ensure proper sealing. Providing a two-component inset may be advantageous to prevent stresses and damage on the cultured tissue caused by the locking mechanism, e.g., the rotation of the lid during the locking step. Providing other numbers of components in an inset may also be useful.

The self-locking lids and insets may be fabricated in polycarbonate (PC), poly(methyl methacrylate) (PMMA) or other thermoplastics materials by CNC micro-milling or injection molding, or in elastomeric materials. In one embodiment, the lid and the insets may have a cylindrical body and four thin teeth (0.6 mm thick, 1.7 mm wide) protruding 1.9 mm from its lateral surface, perpendicularly to the cylinder axis. The body of the lid may be a full cylinder while the body of the inset is a hollow cylinder.

In another embodiment, the inset may be an adaptor for interfacing the organotypic culture to other instrumentation for other applications. For example, the inset may be an interface for transepidermal water loss (TEWL) analysis. The inset may also be an adaptor for an imaging device so the system is compatible with imaging techniques such as Fluorescence Lifetime Imaging and multiphoton microscopy. The inset may also be covered by a customized cap 668, as shown in FIG. 6f, to prevent evaporation or contamination.

FIG. 7 shows a micro-environmental parameter control system. The control system 700 may control the micro-environmental parameters, for example, fluidic control, temperature and humidity control, to create an in vivo like micro-environment. The micro-environment conditions may be fine-tuned for different cultured sample.

The microfluidic chip 720 composing a single-chamber or a multi-chamber device is placed in a customized chip holder 730. The chip holder 730 may be equipped and connected with different components for various parameter controls.

With regards to the fluidic operation, the control system may include one or more independent injectors (not shown) connected to the inlets of each fluidic compartment. The injector provides positive pressure to push the fluid away from the injector. Alternatively, the system may include one or more independent withdrawers (not shown) connected to the outlets of each fluidic compartment. The withdrawer provides negative pressure to pull the fluid towards the withdrawer. In one embodiment, as shown in FIG. 7, culture buffer flow from the inlet 711b to the outlet 712b in the lower compartment. The lower compartment is separated from the upper compartment by a permeable supporting structure 701 with a cell culture or tissue 716. The flow of buffer may be facilitated by an injector connected to the inlet 711*b* or by a withdrawer connected to the outlet 711*b*.

With regards to the temperature control, the control system may include a temperature control module for controlling the temperature in the chip and maintaining the temperature of the fluidic compartments at the temperature suitable for the tissue culture, typically 37° C. For example, a chip holder 730 may have heating elements embedded in it, which embrace the microfluidic chip for temperature control. Plenary heating pipes 752 are inserted between the heating elements 753 (such as a heater) and the chip 720 for uniform temperature distribution in the chip.

With regards to the humidity control, the system may include temperature and humidity control devices for controlling the temperature and the relative humidity of the air that one side of the tissue culture is exposed to. For example, as illustrated in FIG. 7, a thermo-electrical-cooling element (TEC) 756 cools down a cooling plate 755 in a chamber (artificial atmosphere chamber) 754 to condense water vapor in the chamber for relative humidity adjustment in the chamber. The condensed water 758 is removed from the chamber through a slot of heat sink 757 and evaporated to the atmosphere out of the chamber as illustrated by the arrow 759. The heating element 751 inside the chamber is used to stabilize the air temperature at 37° C. In one embodiment, the heating element 751 may be an external heater connected to the chamber.

The air in controlled humidity and temperature is then injected to the chip by a piston pump or peristaltic pump to provide localized air humidity and temperature control above the tissue during culture at the air-liquid interface. For example, the humidity-controlled and temperature-controlled air is injected to the microfluidic chip 720 in the upper compartments for tissue cultures that require an air-liquid interface. The flow of air from the inlet 711*a* to the outlet 712*a* may be facilitated by a piston pump or peristaltic pump connected to the inlet 711*a*. The upper compartments may be covered with a lid 705.

FIG. 8 shows another embodiment of a control system. As shown, the control system 800 includes a localized temperature control for the cultured tissue in the microfluidic chip 820. For example, the heaters 853*a-b* embedded in the chip holder 830 may be controlled via a feed-back loop 863 between a non-contact infrared temperature sensor 861 and the heaters 853*a/b*. The output power of the heater is controlled by pulse width modulation (PWM) signal generated by a microcontroller 862 according to proportional-integral-derivative (PID) algorithm for real-time temperature control in the chip.

The control system 800 may provide an optical window for observation or measurement in the chip. For example, the optical window 864 is positioned below the transparent lower compartment of the chip. The optical window may be structured in the customized chip holder. The optical window further enables optical access to an imaging device 865, for example, a CCD camera, a microscope objective or a photo diode. Other imaging techniques may also be useful. In one embodiment, optically transparent supporting structures and bulk materials are used for the chip to allow real-time and non-invasive imaging with reduced autofluorescence. The lower compartment is separated from the upper compartment by a permeable supporting structure 801 with a cell layer 815.

The microfluidic chip may be used for culturing organotypic tissue in the chip and performing in vitro testing on the cultured organotypic tissue. For example, culturing and testing may include: culturing the organotypic tissue in the microfluidic chip using the inlet channels to supply fresh nutrients according to tissue-specific protocol; identifying the fluidic compartment that serves as application chamber; if necessary, replacing the lid (e.g., 805) with the inset in the fluidic compartment that serves as application chamber; applying the test substance in the said application chamber; perfusing the other fluidic compartment with a suitable buffer solution; collecting the solution coming out of the latter compartment's outlet; and analyzing the collected solution to measure the compound of interest.

Figure 9:
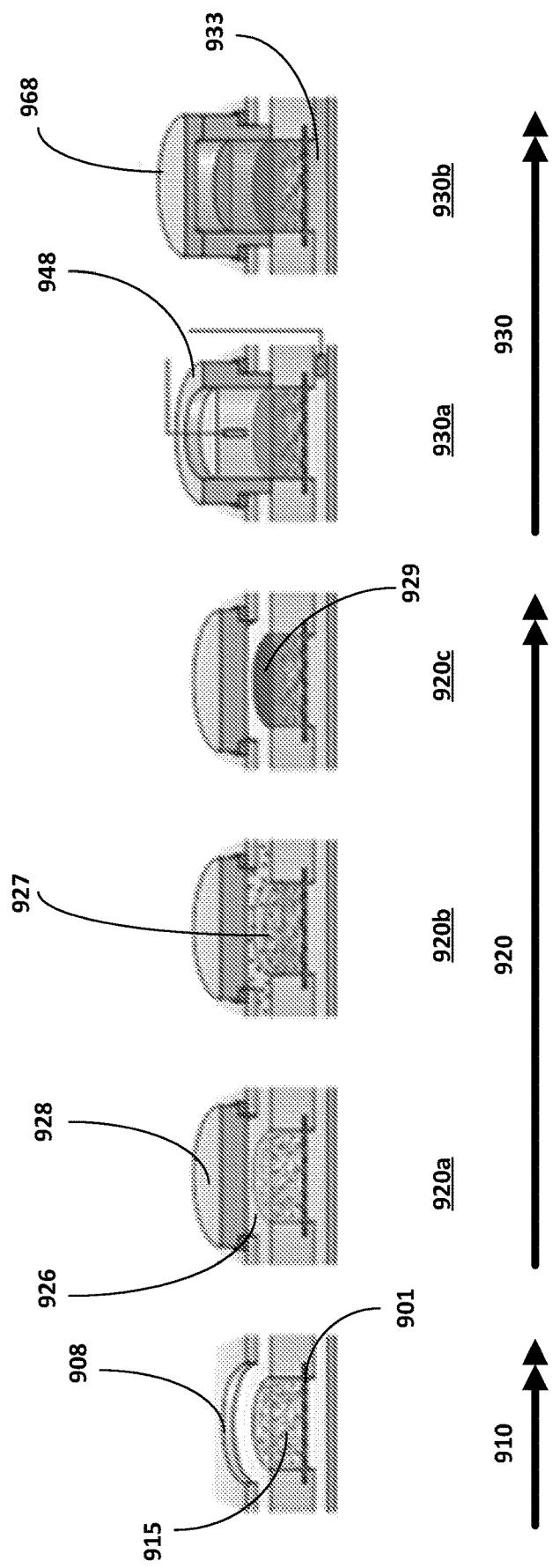
FIG. 9 shows a process for in-situ culturing and for a subsequent in-vitro testing.

FIG. 9 shows an exemplary process flow for a serum-free culturing organotypic skin and for a subsequent in vitro testing. For example, this may include using a microfluidic chip whose microfluidic units have only one access openings in the upper compartment.

Prior to the culture process, the chips, the gaskets, the lids, the insets, the interconnection modules, the tubings and fittings may be sterilized, for example, in autoclave, by UV irradiation or by low energy X-rays irradiation before assembling them on the set-up. The assembled device may further be sterilized, for example, by exposure to UV light for 30 minutes.

At 910, the chip is used as an open system where a gel 915 composed of a mix of extracellular matrix components and dermal cells is cast via the access opening 908 in the culture well of the upper compartment on the permeable supporting structure 901. Other types of cells and respective matrix component may also be useful. For example, cell-laden hydrogels or scaffolds may be cast in the culture chamber through the access opening, while suspended cells may be introduced via the microfluidic channels.

At 920, the chip is used as a bioreactor. At 920*a*, the access opening of the upper compartment is closed with the lid/cover 928. The lid seals the access opening, preventing any media leakage. The lower and upper compartments are perfused with a serum-free dermal culture media 926 for enough days to promote proper development of the dermal component of the skin. At 920*b*, the perfusion of media is interrupted and a suspension of epidermal cells 927 is injected in the upper compartment via the microfluidic channels. Epidermal cells are let precipitate and seed on the dermal gel in the culture well until they adhere to the dermal gel. The lower and upper compartments are then perfused with a serum-free dermal-epidermal culture media until the epidermal cells have reached confluence and cover the dermal gel surface uniformly. At 920*c*, humidity controlled air is infused in the upper compartment to expose the epidermal layer 929 to air while the lower compartment is perfused with a serum-free differentiation media until the development of a full thickness skin equivalent with stratum corneum. The sealing lid ensures an air-tight closure, enabling ventilation and maintenance of the culture at the air-liquid interface. The organotypic skin culture is then completed. Other types of cells and respective culture media may also be useful.

At 930, the lid is replaced with an inset 948 in the upper compartment and the chip is used as an in vitro analysis system. At 930*a* for example, skin integrity evaluation (TEER) is performed. An electrolytic solution is injected in the lower compartment and in the application chamber. Electrodes are submerged in the electrolytic solution in these two compartments, i.e. on the opposite sides of the tissue culture, for measuring the transepidermal electrical resistance. At 930*b*, for example, safety or efficacy assay is performed. A suitable solution is perfused in the lower compartment while dose is applied in the application chamber defined by the inset 948 in the upper compartment. At 930*b*, the inset 948 is covered by a cap 968. For example, the concentration of the molecule of interest is measured in the solution 933 that flows out of the basal chamber of the lower compartment. For example, the measured parameter is the concentration of a molecule of interest present in the lower compartment's solution during the test. The process may be applied to toxicology, irritation, penetration and absorption in vitro tests. Depending on the in vitro test, the compound of interest may be a molecule that diffuses from the application chamber through the organotypic tissue (e.g. in penetration and absorption tests); a molecule secreted by the organotypic tissue in response to the substance applied in the application chamber (e.g. in irritation tests); a post-processing marker of specific cellular conditions (e.g. in toxicology tests); a molecule already present in the initial lower compartment's solution (e.g. in uptake and metabolic studies).

In one embodiment, in the first culturing phase, the fibrin-based dermal equivalent (DE) is cast in the culture chamber of the microfluidic chip and is double-side perfused with serum-free medium at a flow rate of about 1.0 μL/min. Other flow rates may also be useful. In the second phase of culturing phase, after the generation of the DE, keratinocytes were inoculated over the DE apical surface (about $4 \times 10^5$/$cm^2$). Other cell densities may also be useful. The co-culture is double-side perfused with serum-free medium at a flow rate of about 1.0 μL/min. Other flow rates may also be useful. In the third phase of culturing phase, the culture at the air-liquid interface is set-up by interrupting the media perfusion in the upper compartment and connecting the upper compartment to a tubing providing ventilation or humidified air for example by using a peristaltic pump at about 1 μL/min. The lower compartment is perfused with serum-free medium at a flow rate of about 1.0 μL/min to allow differentiation, stratification, and cornification. Other flow rate may also be useful.

Figure 10B:
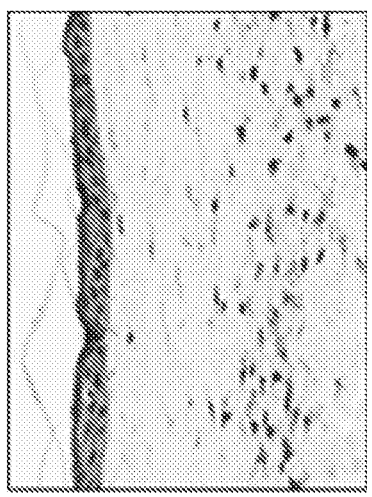
FIGS. 10a-10b show histology sections of organotypic skin reconstructed in the microfluidic chip and in traditional cell culture inserts in 12 well plates.
Figure 10A:
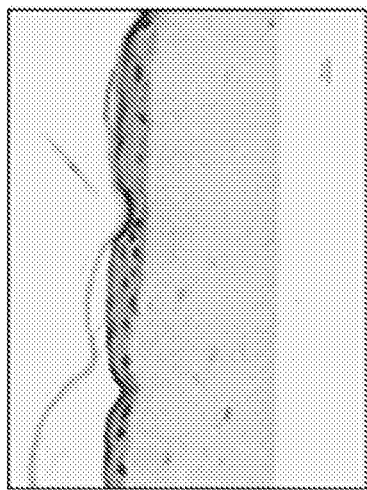

With regards to the skin study, the chip as described yields significant improvements in the quality and functionality of an organotypic skin tissue, including but not limited to, improved epidermal differentiation, a robust epidermal-dermal junction, enhanced barrier functions and lower skin permeability with skin equivalents under dynamic microfluidic culture conditions. FIGS. 10*a*-10*b* show histology sections of organotypic skin reconstructed in the microfluidic chip and in traditional cell culture inserts in 12 well plates. For example, the histology images show full thickness skin equivalent reconstructed using the microfluidic chip (FIG. 10*a*) and on a traditional tissue culture insert in 12 well plates (FIG. 10*b*). Full thickness skin equivalents using a fibrin-based dermal matrix under serum-free culture conditions are reconstructed in the organ-on-chip system (may be referred to as skin-on-chip equivalent or SoCEs). A fibrin-based dermal matrix offers the advantage of culturing complete dermal layer without contraction while serum-free culture conditions reduce the use of animal-derived products and associated batch variability issues. The fibrin matrix provides a natural provisional matrix for establishing cellular architecture by fibroblasts and keratinocytes and results in the production and assembly of a native dermis-like extracellular matrix (ECM). The integrity and barrier function of the SE may be evaluated by measuring the TEER and by conducting permeation experiments on-chip and the results proved that the microfluidic devices and methods disclosed in this patent enhance the SE's barrier function.

The microfluidic chip or skin-on-chip system also has the flexibility to be used for excised human waste skin or other animal skin, including but not limited to porcine skin. The human waste skin has the advantage that it contains the immunologic active cells (Langerhans cells, dermal dendritic cells, some T-lymphocytes, mastocytes) and this could be used to do some specific immunologic staining to predict possible sensitization potential of the tested compounds. The skin absorption and irritation tests may be done under standardized conditions in the same system.

Figure 11B:
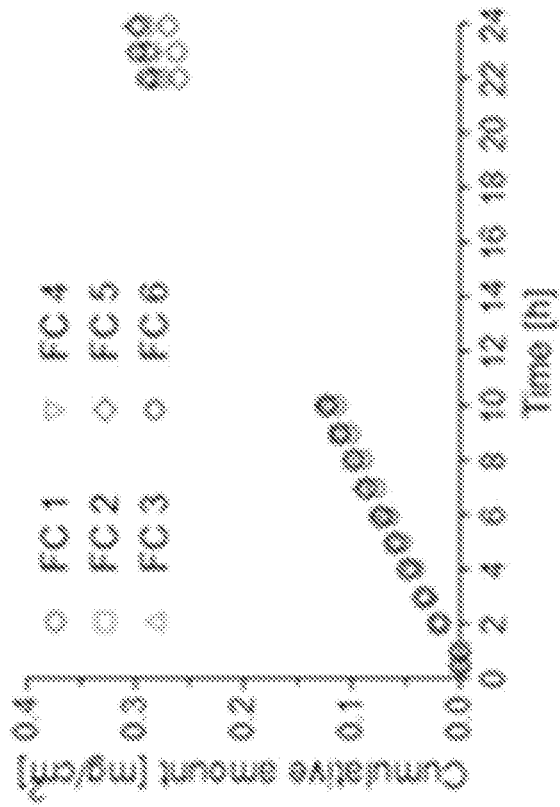
FIGS. 11a-11b show results from a 24-hour diffusion test of an infinite dose of saturated caffeine solution through silicone membranes.
Figure 11A:
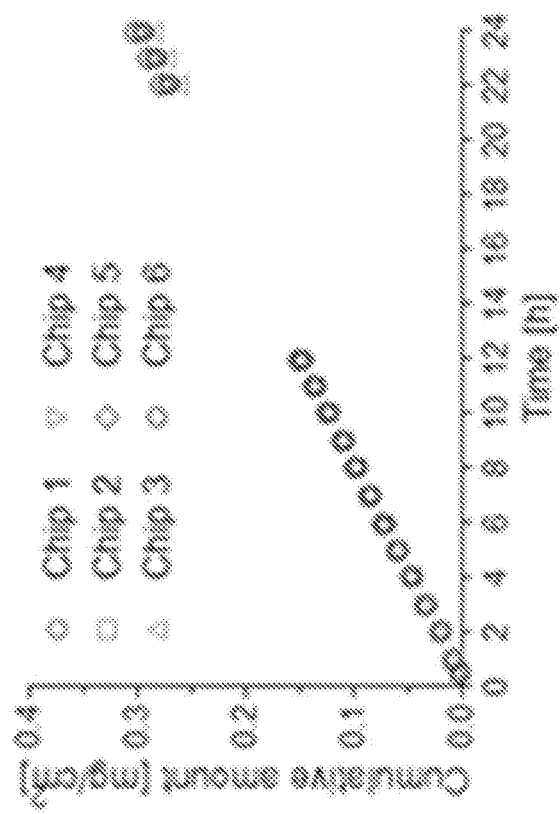

FIGS. 11*a*-11*b* show results from a 24-hour diffusion test of an infinite dose of saturated caffeine solution through silicone membranes (0.54 mm thick) soaked in isopropyl myristate performed on a six chamber microfluidic chip equipped with self-locking insets (FIG. 11*a*) and on six Franz cells (FIG. 11*b*).

As reported in Table 1 below, the steady state flux and the permeability coefficient ($k_p$) estimated from fitting the diffusion profiles from the Franz cells and the diffusion chips coincide. Due to the small receptor volumes in the lower compartment in the chip, the concentrations at the initial time points may be measured and a more reliable estimate of the lag time ($t_{lag}$) may be estimated. Furthermore, smaller coefficient of variation (CV %) values have been observed in the diffusion experiment performed in the microfluidic chip (consistently lower than 3% in all time points): this confirms the improvement in robustness and reliability when using the microfluidic chip for permeation tests.

In addition, the microfluidic chip has the advantage to not excessively dilute the diffused molecule of interest in the receptor chamber. The dilution volume may be controlled by tuning the flow rate in the receptor compartment. This level of miniaturization and control is not available in current diffusion cells technology.

Table 1 shows results from the comparative penetration study: diffusion chips vs. Franz cells.

|  | Diffusion chips | Franz cells |
| --- | --- | --- |
| Steady state flux [μg/cm² h] | 13 | 13 |
| $t_{lag}$ [h] | 0.37 | 0.52 |
| $k_p$ [$10^{-3}$ cm/h] | 0.94 | 0.94 |
| $D_m$ [$10^{-3}$ cm²/h] | 1.8 | 1.3 |
| $k_{m/d}$ | 0.033 | 0.047 | where $t_{lag}$ is the lag time, $k_p$ is the permeability coefficient, $D_m$ is the diffusion coefficient; and $k_{m/d}$ is the partition coefficient.

Figure 12A:
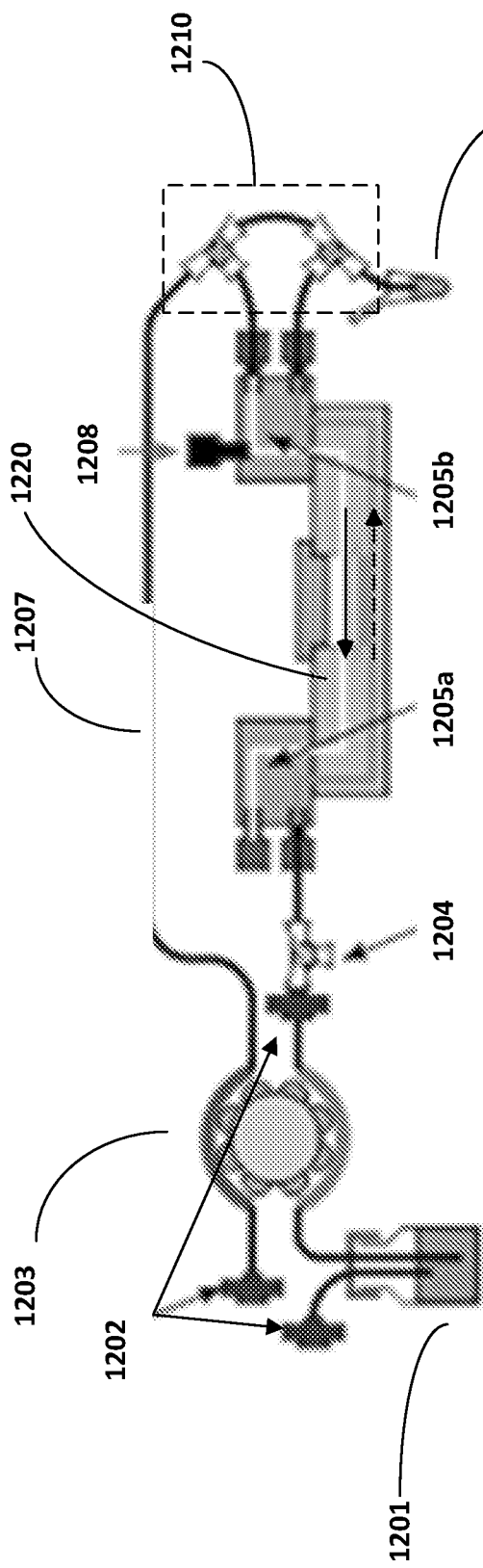
FIGS. 12a-12b show set-ups during the in-situ organotypic culturing process and during the in-vitro testing process.
Figure 12B:
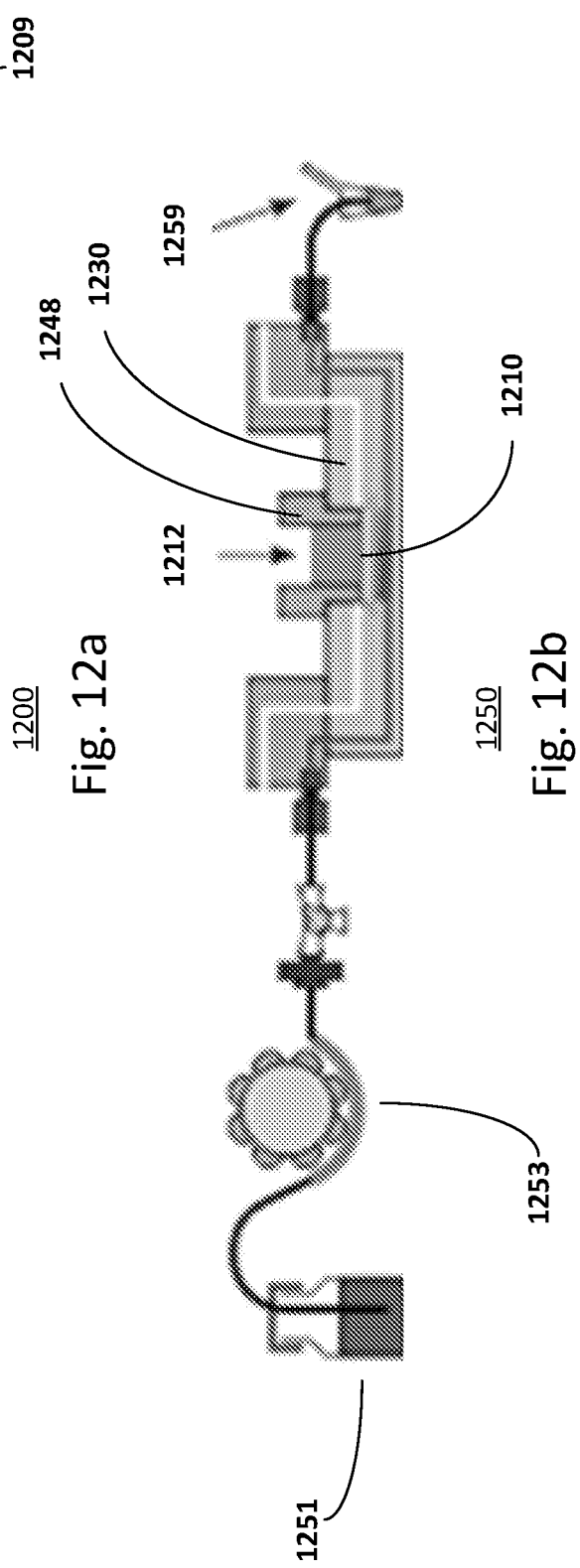

FIGS. 12*a*-12*b* show set-ups during the in situ organotypic culturing process and during the in vitro testing process. Customized add-on modules attached to the chip and aligned with the inlets and outlets provide the macro-to-micro interconnections with the tubings and with the external experimental setup. Although the set-ups are illustrated with 2-compartment chips, it is understood that other configurations of experimental set-ups with different embodiments of microfluidic chips may also be useful.

FIG. 12*a* shows an experimental set-up 1200 during the skin culture process with a closed lid 2-compartment microchip 1220. The arrow with a solid line indicates the direction of the flow of air in the upper compartment and the arrow with a dotted line indicates the direction of the flow of culture media in the lower compartment. Culture media is provided from a media reservoir container 1201 and is pumped, for example by a peristaltic pump 1203, via a filter 1202 and a 3-way valve 1204 to the inlet of the lower compartment of the chip. The valve system 1210 is assembled to enable selective switching from a double-side perfusion setup during the first two culturing phases, to a fluidic configuration that coupled controlled ventilation of the upper compartment with perfusion in the lower compartment. Perfusates are then collected at a container 1209 via the outlet channel of the lower compartment of the chip for downstream characterization and quantification. For example, the container 1209 may be a vial, a tube, the well of a 96 well plate, the well of a 12 well plate. The media is filtered using sterile syringe filters 1202 with a pore size of 0.2 µm when injected into the reservoir and before entering the microfluidic chip.

As for the upper compartment, ventilation is provided via the ventilation tubings 1207 with the aid of a filter 1202, the peristalitic pump 1203 and interconnection modules 1205a-b. The interconnection modules 1205a-b may be add-on modules or be part of a chip holder. Keratinocyte is inoculated in the upper compartment of the chip at the entrance point 1208.

FIG. 12b shows an experimental set-up 1250 during a permeation test with a 2-compartment microchip 1230 with an inset 1248. Buffer is provided from a buffer reservoir container 1251 and is pumped, for example by a peristalitic pump 1253, via a filter and a valve to the inlet of the lower compartment of the chip. Testing substance 1212 is applied at the application chamber defined by the inset 1248 at the upper compartment of the chip. Testing substance is then permeated through the tissue and the permeable supporting structure 1210. The buffer with permeated testing substance is then collected at a container 1259 via the outlet channel of the lower compartment of the chip. For example, the container 1209 may be a vial, a tube, the well of a 96 well plate, the well of a 12 well plate. The collected solution is then analyzed to measure the compound of interest.

For large numbers of doses, treatments and controls, the throughput may be easily increased by using multiple copies of the microfluidic chip, or by adapting the chip design to accommodate additional culture chambers. For example, the microfluidic chip may be adapted to a multi-well plate format, where the microfluidic unit may be reproduced.

In one embodiment, the customized macro-to-micro interconnection modules may be designed and fabricated by CNC micro-milling or injection molding. The macro-to-micro interconnection modules connect the inlet and outlet channels of the chips to tubings via fittings. Each interconnection module contains 8 macro-to-micro fluidic ports regularly spaced as the wells of a 96-well plate. The interconnection module designed for the outlets of the organ-on-chip device includes an additional fitting for the inoculation of cells which is closed with a plug when not used.

In one embodiment, several cell types may be introduced in the different compartments to add levels of complexity to the in vitro model. Naturally residing cell types in the skin appendages or immune cells may be introduced in the relevant compartments to add levels of complexity to the in vitro model for migration, immunology and inflammation studies. In one example, immune cells may be introduced in the lower compartment to study their migration pattern and response to certain stimuli. In another example, endothelial cells may be introduced in the lower compartment so that the cell layer formed on the lower side of the permeable support membrane may mimic the walls of the blood vessels. In yet another example, bacteria may be introduced in the upper compartment to create a tissue-specific microbiome model. Furthermore, the chip may be scaled to reconstruct tissues and organs in a high-throughput and/or multi-organ approach.

Figure 13:
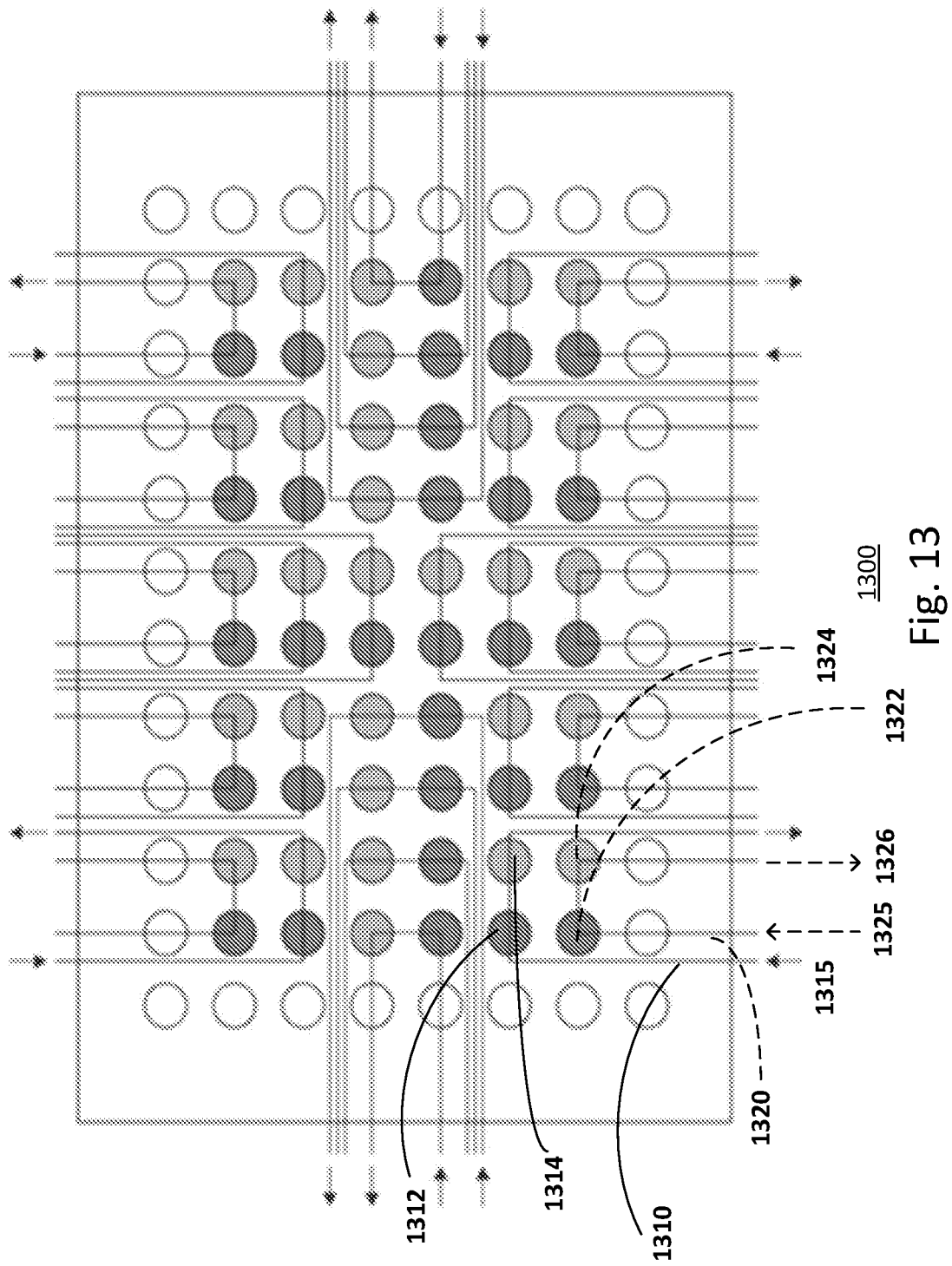
FIG. 13 shows an embodiment of a high-throughput microfluidic chip.

FIG. 13 shows an exemplary embodiment of a high-throughput microfluidic chip 1300. For example, the microfluidic chip may be adapted to a 96-well plate format with 10 or more microfluidic units. The microfluidic unit includes a cell culture chamber and a chamber for in-line detection. For example, following the line 1310 and the arrow direction, fluid is introduced to the chip via inlet channel 1315. The first well 1312 may be a cell culture chamber which is similar to the one in the chip described in FIG. 12a. The second well 1314 may be used for in-line detection and measurement of the compound of interest. Each line represents one microfluidic unit. For example, following the dotted line 1320, the second unit includes a second inlet channel 1325, a second cell culture chamber 1322, a second well for in-line detection 1324, and a second outlet channel 1326. This configuration is advantageous because may combine toxicity evaluation of the organotypic culture (via imaging of the culture) with the penetration or irritation analysis performed in the detection chamber using, for example, a spectrophotometer.

Multiple chambers may also be used to culture different organs in parallel and to connect them in series for multi-organ studies.

Figure 14:
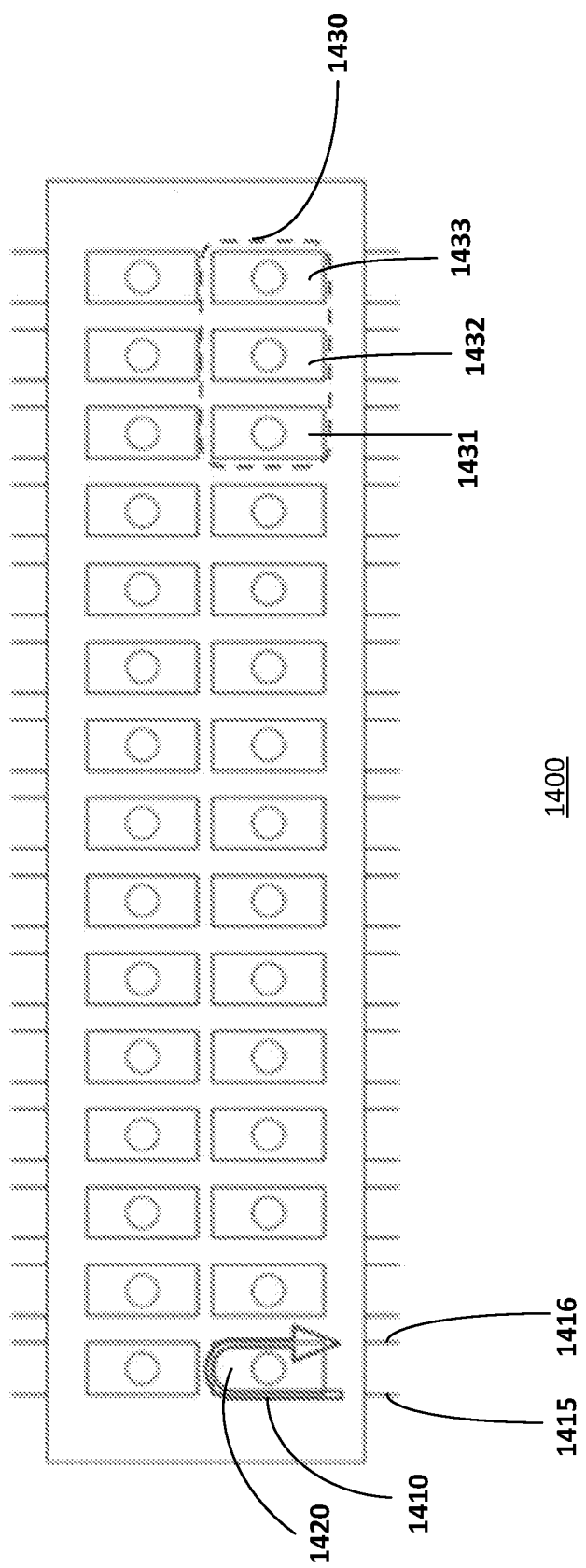
FIG. 14 shows yet another embodiment of a high-throughput microfluidic chip.

FIG. 14 shows yet another embodiment of a high-throughput microfluidic chip. For example, the microfluidic chip 1400 is a high-throughput chip capable of testing at least 10 compounds in triplicates in parallel. For example, following the arrow 1410, each microfluidic unit includes the inlet channel 1415, the culture/testing chamber 1420 and the outlet channel 1416. The microfluidic unit may be grouped for different applications. For example, three individual microfluidic units 1431, 1432 and 1433 may be grouped for the same application as a triplicate 1430. In an embodiment, 30 individual chips are arranged in 2×15 configuration and 3 adjacent chips on the same row are arranged as 1 triplicate. The triplicate will be discussed further in FIGS. 15a-15b.

Although the high-throughput microfluidic chips are illustrated with a 96-well plate format with 30 times of the microfluidic unit (as shown in FIG. 13) and with a chip capable of testing 10 compounds in triplicates in parallel (as shown in FIG. 14), it is understood that other configurations of the high-throughput microfluidic chips may also be useful. The configuration of the high-throughput microfluidic chip depends on the position and location of the inlets and outlets.

Figure 15A:
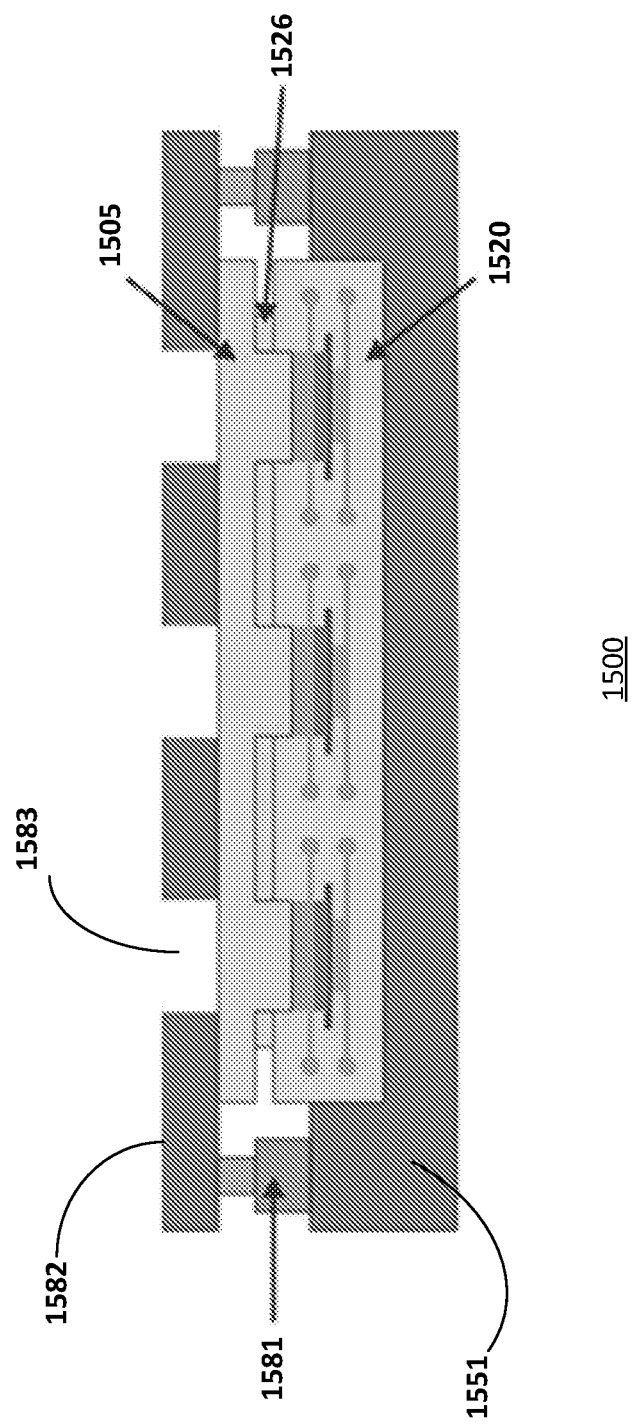
FIGS. 15a-15b show embodiments of triplicates of microfluidic chips with a multi-lid and a multi-inset.
Figure 15B:
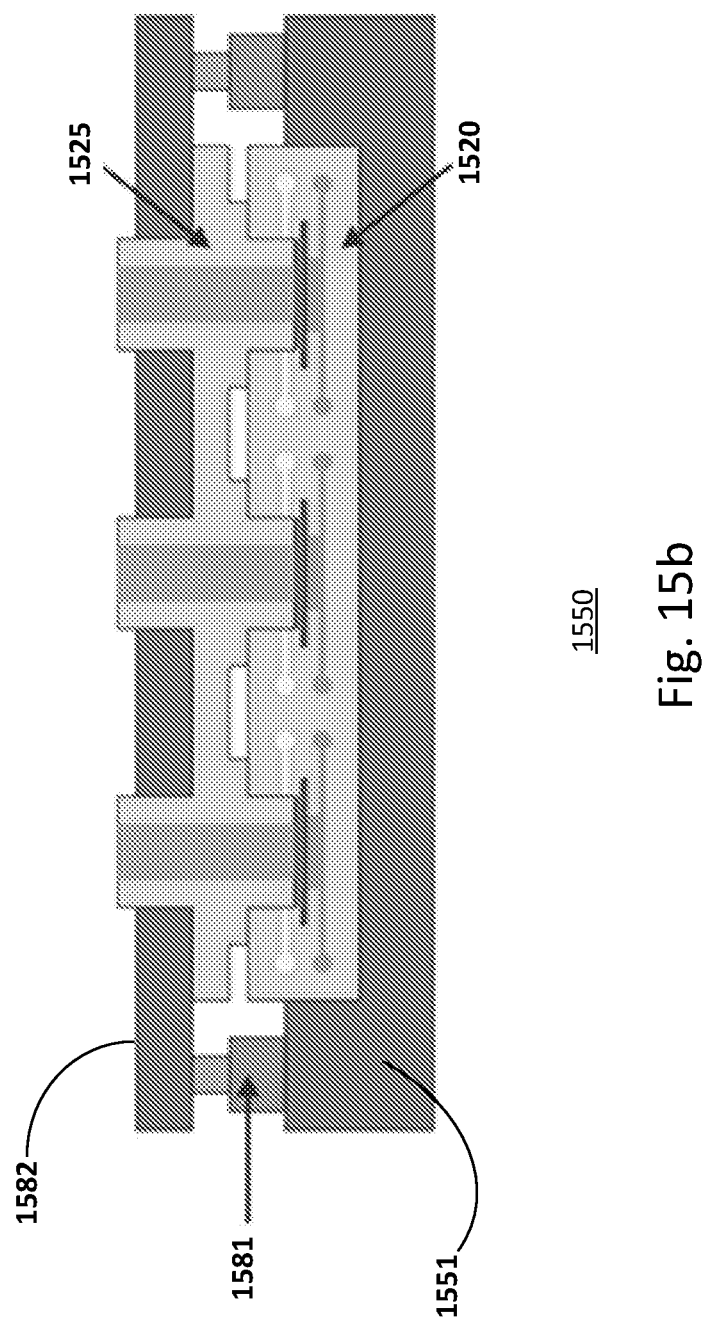

FIGS. 15a-15b show various embodiments of the lid/cover and insets for high-throughput chips. For example, FIG. 15a shows an embodiment 1500 with a multi-lid cover. The microfluidic chip illustrated as a triplicate configuration 1520 is placed in the customized holder 1551.

The cover 1505 may be made of soft materials with intrinsic sealing properties (silicone rubbers, PDMS, etc.). For example, the multi-lid cover may be formed of a soft polymer. Other types of pliable material which may form a seal may also be useful. In another embodiment, the cover 1505 may be made of a hard material, such as thermoplastic materials. The covers made with hard materials may be equipped with a sealing gasket 1526 for a proper sealing of the access opening.

A clamper or clamping mechanism provides the adequate force to the clamping plate for sealing the multi-lid cover to the access openings. For example, a clamping plate 1582 made of hard materials (metals or hard polymers) is placed over the cover 1505 and a clamping mechanism 1581 joint to the clamping plate provides the necessary force for sealing the cover to the access openings. The clamping plate 1582 may contain windows 1583 in correspondence of the culture chambers in order to allow microscopy observations and compatibility with different multi-insets cover designs. The clamping mechanism 1581 may include various features (not shown) such as a set of mechanical clamps; a set of springs; a set of screws and nuts; a set of magnets; a vacuum chamber; or a set of stepper motor that moves and keep the clamping plate down on the cover or vice versa. These features are spatially arranged in order to provide a uniform application of the clamping force.

The clamping mechanism allows lifting and clamping of the clamping plate for swopping the multi-lid cover used during the cell culture process and the multi-inset cover that may be used during the testing phase. FIG. 15b shows an embodiment 1550 of a microfluidic chip as a triplicate configuration with a multi-inset cover 1525. The set-up is similar to that described in FIG. 15a, common elements may not be described or described in detail. The multi-inset cover 1525 may be made of soft materials with intrinsic sealing properties (silicone rubbers, PDMS, etc.). The multi-inset cover 1525 may be made of a hard material, such as thermoplastic materials. The covers made with hard materials may be equipped with a gasket (not shown) for a proper sealing of the access opening.

To summarize, a microfluidic chip includes at least one microfluidic unit which includes two fluidic compartments separated by a permeable supporting structure that acts as a support for the organotypic culture, scaffold or excised tissue. The fluidic compartments may have an access opening that may be closed by a lid. The microfluidic chip may be used for in vitro testing using a set of interchangeable lid/cover and insets.

The microfluidic chip may be used in an environmental control system for exposing the organotypic culture to a controlled climate, such as a gaseous fluid or gaseous mixtures with adjustable temperature and humidity.

The access opening in the fluidic compartment may be closed and opened. A set of interchangeable lid/cover and inset for the access opening enables seamless continuation of in vitro test, compatible with current in vitro test methods and detection technology, on the tissue cultured directly in the system without any movement, handling and/or manipulation of the tissue and with minimum interference to the culture environment.

The microfluidic chip as described in this disclosure results in various advantages. For example, the chip avoids adsorption of lipophilic chemicals that is generally associated with PDMS. The chip also shows high precision in the estimation of transport parameters of model compounds as well as a significant reduction in the unstirred water layer effect. The chip is an integrated culturing and testing microfluidic device which enables the entire culture process and downstream functional assays to be conducted in the same microfluidic platform. Furthermore, the chip is suitable for mass production and therefore is a cost effective microfluidic platform. For example, the chip is suitable for high-throughput in situ permeability and toxicity testing. In addition, a large-scale translation of this dynamic perfusion and ventilation microfluidic chip may be potential for tissue regeneration and wound healing applications in a shorter time frame.

The inventive concept of the present disclosure may be embodied in other specific forms without departing from the spirit or essential characteristics thereof. The foregoing embodiments, therefore, are to be considered in all respects illustrative rather than limiting the invention described herein. The scope of the invention is thus indicated by the appended claims, rather than by the foregoing description, and all changes that come within the meaning and range of equivalency of the claims are intended to be embraced therein.

What is claimed is:

1. A microfluidic chip comprising:
a chip body having first and second major surfaces;
a cavity disposed in the chip body, the cavity comprises
a first cavity access opening disposed on the first major surface for accessing the cavity,
a permeable support having first and second support surfaces, the permeable support is structured in the cavity and separates the cavity into first and second fluidic compartments, the first support surface forms a part of the first fluidic compartment and the second support surface forms a part of the second fluidic compartment, wherein the first support surface is adapted to support a first sample for testing provided through the first cavity access opening, the first fluidic compartment is disposed proximate to the first major surface of the chip body, and
the second fluidic compartment is disposed proximate to the second major surface of the chip body;
a first set of fluidic channels in fluidic communication with the first fluidic compartment, the first set of fluidic channels having at least one first inlet channel and at least one first outlet channel, wherein the at least one first inlet channel and the at least one first outlet channel are arranged laterally spaced apart from one another with the first fluidic compartment arranged between the at least one first inlet channel and the at least one first outlet channel, the at least one first inlet channel and the at least one first outlet channel being arranged away and independent from the second fluidic compartment, such that the first set of fluidic channels is adapted to flow a first medium into the first fluidic compartment via the first inlet channel and out the first fluidic compartment via the first outlet channel; and
a second set of fluidic channels in fluidic communication with the second fluidic compartment, the second set of fluidic channels having at least one second inlet channel and at least one second outlet channel, wherein the at least one second inlet channel and the at least one second outlet channel are arranged laterally spaced apart from one another with the second fluidic compartment arranged between the at least one second inlet channel and the at least one second outlet channel, the at least one second inlet channel and the at least one second outlet channel being arranged away and independent from the first fluidic compartment, such that the second set of fluidic channels is adapted to flow a second medium into the second fluidic compartment via the second inlet channel and out the second fluidic compartment via the second outlet channel,
wherein in operation, the first medium flows through the first fluidic compartment independently from the second medium flowing through the second fluidic compartments.

2. The microfluidic chip of claim 1 comprises a lid, wherein the lid is arranged to cover over and seal the first cavity access opening.

3. The microfluidic chip of claim 2 wherein the first set of fluidic channels in fluidic communication with the first fluidic compartment is disposed on a lid surface of the lid.

4. The microfluidic chip of claim 2 wherein the first set of fluidic channels in fluidic communication with the first fluidic compartment comprises:

a first subset of first fluidic channels disposed in the microfluidic chip body, the first subset of first fluidic channels having at least one first subset inlet channel and at least one first subset outlet channel; and a second subset of first fluidic channels, the second subset of first fluidic channels having at least one second subset inlet channel and at least one second subset outlet channel, the second subset of first fluidic channels being disposed on a lid surface of the lid.

5. The microfluidic chip of claim 2 wherein the lid comprises:

an inset portion insertable into the first cavity access opening to block the first set of fluidic channels in fluidic communication with the first fluidic compartment; and a lid set of fluidic channels disposed on a lid surface of the lid, wherein the lid set of fluidic channels comprises at least one first lid inlet channel and at least one first lid outlet channel, the lid set of fluidic channels is adapted to flow the first medium into the first fluidic compartment via the first lid inlet channel and out the first fluidic compartment via the first lid outlet channel.

6. The microfluidic chip of claim 2 wherein the lid comprises a mechanical lid which is mechanically mounted to the first cavity access opening.

7. The microfluidic chip of claim 1 comprises a lid inset, wherein the lid inset includes an inset portion insertable into the first cavity access opening, at least part of the first cavity access opening arranged to surround the inset portion, and a bottom of the lid inset is adapted to fix a sample in position on the permeable support for testing.

8. The microfluidic chip of claim 7 wherein the lid inset includes a lid surface for sealing the first cavity access opening.

9. The microfluidic chip of claim 8 wherein:

the inset portion of the lid blocks the first set of fluidic channels in fluidic communication with the first fluidic compartment; and the lid surface comprises a lid set of fluidic channels disposed on the lid surface of the lid, wherein the lid set of fluidic channels comprises at least one first lid inlet channel and at least one first lid outlet channel, the lid set of fluidic channels is adapted to flow the first medium into the first fluidic compartment via the first lid inlet channel and out the first fluidic compartment via the first lid outlet channel.

10. The microfluidic chip of claim 1 wherein the first fluidic compartment serves as a culturing chamber comprising:

a first section which serves as an apical sub-chamber, the first section is disposed proximate to the first cavity access opening;

a second section which serves as a basal sub-chamber, the second section is disposed between the first section and adjacent to the first section and the permeable support, the permeable support serves as a base of the basal sub-chamber; and wherein
dimensions of the first and second sections are different, and
the first and second sections facilitate a multi-layered co-culture.

11. The microfluidic chip of claim 1 wherein:

the cavity comprises a second cavity access opening on the second major surface of the chip body, the second cavity access opening provides access to the second fluidic compartment; and the second support surface is adapted to support a second sample for testing provided through the second cavity access opening.

12. The microfluidic chip of claim 11 comprises:

a first lid for sealing the first cavity access opening on the first major surface of the chip body; and a second lid for sealing the second cavity access opening on the second major surface of the chip body.

13. The microfluidic chip of claim 11 comprises:

a first set of first access ports in fluidic communication with the first set of fluidic channels; and a second set of second access ports in fluidic communication with the second set of fluidic channels.

14. The microfluidic chip of claim 1 wherein the chip body includes a multi-piece chip body comprising:

a first member, the first member includes first and second first major surfaces, the first member defines the first major surface of the chip body, the first member includes a first member opening through the major surfaces of the first member;

a first intermediate member having first and second major surfaces, the first intermediate member includes
a first intermediate member opening through the major surfaces of the first intermediate member,
the first set of first fluidic channels in communication with the first intermediate member opening, and
a first major surface of the first intermediate member is mated with the second major surface of the first member, wherein the first member opening and the first intermediate member form the first fluidic compartment of the chip body;

a permeable support member;

a second intermediate member having first and second major surfaces, the second member includes
a second intermediate member opening through the major surfaces of the second intermediate member, the second intermediate member forms the second fluidic compartment,
the second set of fluidic channels in fluidic communication with the second intermediate member opening, the second set of fluidic channels isolated from the first set of fluidic channels, and
a first major surface of the second intermediate member is mated with the second major surface of the first intermediate member, wherein the permeable support member is disposed between the first and second intermediate members, the permeable support member separates the first fluidic compartment from the second fluidic compartment formed by the second intermediate member opening; and a second member having first and second major surfaces, wherein the second major surface of the second member defines the second major surface of the chip body, and the first major surface is mated to the second major surface of the second intermediate member.

15. The microfluidic chip of claim 1 is a high throughput microfluidic chip comprising:

a plurality of the cavities disposed in the chip body having access openings on the first major surface of the chip body, wherein each cavity comprises
first and second fluidic compartments separated by a permeable support, wherein the first fluidic compartment is proximate to the access opening on the first major surface of the chip body,
a first set of fluidic channels in communication with the first fluidic compartment, a second set of fluidic channels in communication with the second fluidic compartment, and an access opening in communication with the first fluidic compartment on the first major surface of the chip body;

a multi-lid cover adapted to fit into the access openings of the cavities on the first major surface of the chip body; and a mounter for mounting the multi-lid cover on the first major surface of the chip body.

16. The microfluidic chip of claim 1 further comprising an environmental control system, wherein the environmental control system comprising:

a test chamber;

a chip holder in the test chamber, the chip holder adapted for a microfluidic chip to be mounted thereon, wherein the microfluidic chip comprises a chip body having a cavity disposed in the chip body, a permeable support separating the cavity into first and second fluidic compartments, wherein the chip body comprises a first cavity access opening for accessing the first fluidic compartment, a first set of fluidic channels in fluidic communication with the first fluidic compartment, the first set of fluidic channels having at least one first inlet channel and at least one first outlet channel, the first set of fluidic channels is adapted to flow a first fluid into the first fluidic compartment via the first inlet channel and out the first fluidic compartment via the first outlet channel, and a second set of fluidic channels in fluidic communication with the second fluidic compartment, the second set of fluidic channels having at least one second inlet channel and at least one second outlet channel, the second set of fluidic channels is adapted to flow a second fluid into the second fluidic compartment via the second inlet channel and out the second fluidic compartment via the second outlet channel;

a chip temperature control unit in the chip holder for controlling a temperature of the microfluidic chip when mounted onto the chip holder; and a thermal-electrical-cooling unit for controlling humidity of an atmosphere in the test chamber.

17. The microfluidic chip of claim 1, wherein the first cavity access opening is arranged opposite to the permeable support.

* * * * *